US011084851B2

(12) United States Patent
Bian et al.

(10) Patent No.: US 11,084,851 B2
(45) Date of Patent: *Aug. 10, 2021

(54) CAUSTIC STABLE CHROMATOGRAPHY LIGANDS

(71) Applicant: EMD Millipore Corporation, Burlington, MA (US)

(72) Inventors: Nanying Bian, Lexington, MA (US); Neil Soice, Newbury Park, CA (US); Shari Spector, Lexington, MA (US); Kara Levine, Worcester, MA (US)

(73) Assignee: EMD MILLIPORE CORPORATION, Burlington, MA (US)

( * ) Notice: Subject to any disclaimer, the term of this patent is extended or adjusted under 35 U.S.C. 154(b) by 473 days.

This patent is subject to a terminal disclaimer.

(21) Appl. No.: 16/113,403

(22) Filed: Aug. 27, 2018

(65) Prior Publication Data

US 2018/0362595 A1 Dec. 20, 2018

Related U.S. Application Data

(63) Continuation of application No. 12/653,888, filed on Dec. 18, 2009, now Pat. No. 10,072,050.

(60) Provisional application No. 61/203,664, filed on Dec. 24, 2008.

(51) Int. Cl.
*C07K 14/31* (2006.01)
*B01D 15/38* (2006.01)
*B01J 20/286* (2006.01)
*B01J 20/32* (2006.01)

(52) U.S. Cl.
CPC .......... *C07K 14/31* (2013.01); *B01D 15/3809* (2013.01); *B01J 20/286* (2013.01); *B01J 20/3244* (2013.01); *B01J 20/3274* (2013.01)

(58) Field of Classification Search
CPC combination set(s) only.
See application file for complete search history.

(56) References Cited

U.S. PATENT DOCUMENTS

| 4,617,266 | A | 10/1986 | Fahnestock |
| 4,879,378 | A | 11/1989 | Foster et al. |
| 5,084,559 | A | 1/1992 | Profy |
| 5,143,844 | A | 9/1992 | Abrahmsen et al. |
| 5,151,350 | A | 9/1992 | Colbert et al. |
| 5,198,531 | A | 3/1993 | Webber et al. |
| 5,240,680 | A | 8/1993 | Zuckermann et al. |
| 5,260,373 | A | 11/1993 | Profy et al. |
| 5,580,757 | A | 12/1996 | Desnick et al. |
| 6,013,763 | A | 1/2000 | Braisted et al. |
| 6,060,596 | A | 5/2000 | Lerner et al. |
| 6,197,927 | B1 | 3/2001 | Braisted et al. |
| 6,399,750 | B1 | 6/2002 | Johansson |
| 6,602,977 | B1 | 8/2003 | Ljungqvist et al. |
| 6,831,161 | B1 | 12/2004 | Uhlen et al. |
| 7,026,446 | B1 | 4/2006 | Atwell et al. |
| 7,083,948 | B1 | 8/2006 | Sassenfeld et al. |
| 7,163,686 | B1 | 1/2007 | Silverman |
| 7,192,738 | B2 | 3/2007 | Lowman et al. |
| 7,311,918 | B2 | 12/2007 | Choi et al. |
| 7,691,608 | B2 | 4/2010 | Peyser |
| 7,709,209 | B2 | 5/2010 | Hober et al. |
| 7,833,723 | B2 | 11/2010 | Bian et al. |
| 7,834,158 | B2 | 11/2010 | Hober |
| 7,846,682 | B2 | 12/2010 | Bian et al. |
| 7,847,071 | B2 | 12/2010 | Bonnerjea et al. |
| 8,329,860 | B2 | 12/2012 | Hall et al. |
| 8,592,555 | B2 | 11/2013 | Spector |
| 8,754,196 | B2 | 6/2014 | Spector et al. |
| 8,895,706 | B2 * | 11/2014 | Spector ............... B01J 20/3272 530/402 |
| 9,018,305 | B2 * | 4/2015 | Spector .................. C07K 14/31 525/54.1 |
| 9,234,010 | B2 * | 1/2016 | Spector .................. C07K 14/31 |
| 9,376,474 | B1 * | 6/2016 | Spector .................. C07K 14/31 |
| 9,920,112 | B2 * | 3/2018 | Spector .................... C07K 1/22 |
| 10,072,050 | B2 * | 9/2018 | Bian .................... B01J 20/3274 |
| 2003/0059910 | A1 | 3/2003 | Moloney et al. |
| 2005/0100970 | A1 | 5/2005 | Uhlen et al. |
| 2005/0143566 | A1 | 6/2005 | Hober |
| 2005/0171339 | A1 | 8/2005 | Sugo et al. |
| 2006/0030696 | A1 | 2/2006 | Bonnerjea et al. |
| 2006/0134805 | A1 | 6/2006 | Berg et al. |

(Continued)

FOREIGN PATENT DOCUMENTS

| CN | 1642976 A | 7/2005 |
| CN | 1649894 A | 8/2005 |

(Continued)

OTHER PUBLICATIONS

Linhult et al., "Mutational Analysis of the Interaction Between Albumin-Binding Domain from Streptococcal Protein G and Human Serum Albumin", Protein Science vol. 11, 2002, pp. 206-213.
Ljungberg et al., "The Interaction Between Different Domains of Staphylococcal Protein A and Human Polyclonal IgG, IgA, IgM And F(ab')2: Separation of Affinity from Specificity", Molecular Immunology, vol. 30, No. 14, 1993, pp. 1279-1285.
Ljungquist et al., "Thiol-Directed Immobilization of Recombinant IgG-Binding Receptors", European Journal of Biochemistry, vol. 186, No. 3, Dec. 22, 1989, pp. 557-561.
McKerrow et al., "Deamidation Of Asparaginyl Residues as a Hazard in Experimental Protein and Peptide Procedures", Department of Biology, University of California, San Diego, Dec. 1, 1970, pp. 565-568.

(Continued)

*Primary Examiner* — Daniel E Kolker
*Assistant Examiner* — James L Rogers
(74) *Attorney, Agent, or Firm* — EMD Millipore Corporation

(57) ABSTRACT

The present invention relates to chromatography ligands having improved caustic stability, e.g., ligands based on immunoglobulin-binding proteins such as, Staphylococcal protein A, as well as methods of making and using such ligands.

11 Claims, 12 Drawing Sheets

Specification includes a Sequence Listing.

(56) References Cited

U.S. PATENT DOCUMENTS

| | | |
|---|---|---|
| 2006/0194950 A1 | 8/2006 | Hober et al. |
| 2006/0194955 A1 | 8/2006 | Hober et al. |
| 2006/0205016 A1 | 9/2006 | Silverman |
| 2007/0207500 A1 | 9/2007 | Bian et al. |
| 2008/0096819 A1 | 4/2008 | Grabstein et al. |
| 2008/0108053 A1 | 5/2008 | Patchornik |
| 2008/0210615 A1 | 9/2008 | Joehnck et al. |
| 2008/0255027 A1 | 10/2008 | Moya et al. |
| 2008/0312425 A1 | 12/2008 | Bonnerjea et al. |
| 2009/0093017 A1 | 4/2009 | Peyser |
| 2009/0246885 A1 | 10/2009 | Bian et al. |
| 2009/0299035 A1 | 12/2009 | Iwakura et al. |
| 2009/0317381 A1 | 12/2009 | Plaut et al. |
| 2010/0022760 A1 | 1/2010 | Hober et al. |
| 2010/0048876 A1 | 2/2010 | Hall et al. |
| 2010/0063256 A1 | 3/2010 | Spector |
| 2010/0130721 A1 | 5/2010 | Iwakura et al. |
| 2010/0168395 A1 | 7/2010 | Sato |
| 2010/0221844 A1 | 9/2010 | Bian et al. |
| 2010/0286373 A1 | 11/2010 | Majima et al. |
| 2012/0149875 A1 | 6/2012 | Johansson et al. |
| 2014/0046037 A1 | 2/2014 | Spector |

FOREIGN PATENT DOCUMENTS

| | | |
|---|---|---|
| CN | 101522278 A | 9/2009 |
| CN | 101704879 A | 5/2010 |
| CN | 101775069 A | 7/2010 |
| CN | 108912216 A | 11/2018 |
| EP | 0230869 A2 | 8/1987 |
| EP | 0550771 A1 | 7/1993 |
| EP | 1564286 A1 | 8/2005 |
| EP | 1123389 B1 | 10/2005 |
| EP | 1601697 B1 | 5/2007 |
| EP | 1972689 A2 | 9/2008 |
| EP | 1992692 A1 | 11/2008 |
| EP | 2014359 A1 | 1/2009 |
| EP | 2066419 A1 | 6/2009 |
| EP | 2157099 A1 | 2/2010 |
| EP | 2202310 A2 | 6/2010 |
| JP | 2005-220028 A | 8/2005 |
| JP | 2005-538693 A | 12/2005 |
| JP | 2006-304633 A | 11/2006 |
| JP | 2007-525412 A | 9/2007 |
| JP | 2007-252368 A | 10/2007 |
| JP | 2007-537700 A | 12/2007 |
| JP | 2008-255046 A | 10/2008 |
| JP | 2009-071766 A | 4/2009 |
| JP | 5480558 B2 | 4/2014 |
| RU | 2415865 C2 | 4/2011 |
| WO | 84/00773 A1 | 3/1984 |
| WO | 90/02182 A1 | 3/1990 |
| WO | 90/09237 A1 | 8/1990 |
| WO | 95/19374 A1 | 7/1995 |
| WO | 97/17361 A1 | 5/1997 |
| WO | 97/36614 A1 | 10/1997 |
| WO | 00/23580 A1 | 4/2000 |
| WO | 00/63243 A1 | 10/2000 |
| WO | 00/69457 A1 | 11/2000 |
| WO | 03/080655 A1 | 10/2003 |
| WO | 2004/076485 A1 | 9/2004 |
| WO | 2005/003156 A1 | 1/2005 |
| WO | 2006/004067 A1 | 1/2006 |
| WO | 2006/070416 A1 | 7/2006 |
| WO | 2006/092338 A2 | 9/2006 |
| WO | 2007/019376 A2 | 2/2007 |
| WO | 2007/138328 A2 | 12/2007 |
| WO | 2008/039141 A1 | 4/2008 |
| WO | 2008/091740 A2 | 7/2008 |
| WO | 2008/127457 A2 | 10/2008 |
| WO | 2009/138484 A2 | 11/2009 |
| WO | 2009/146755 A1 | 12/2009 |
| WO | 2010/080065 A1 | 7/2010 |
| WO | 2010/110288 A1 | 9/2010 |
| WO | 2012/074463 A1 | 6/2012 |
| WO | 2012/087230 A1 | 6/2012 |

OTHER PUBLICATIONS

McKerrow et al., "Primary Sequence Dependence of the Deamidation of Rabbit Muscle Aldolase", Bonner Laboratory of Biology and Chemistry University of California, San Diego, Jan. 11, 1974, 1 page.

Rodwell, "Structure and Functions of Proteins and Enzymes", Amino Acids, pp. 23-28.

Needleman et al., "A General Method Applicable to the Search for Similarities in the Amino Acid Sequence of Two Proteins", Journal Of Molecular Biology vol. 48, 1970, pp. 443-453.

Nilsson et al., "A Synthetic IgG-Binding Domain Based on Staphylococcal Protein A", Protein Engineering vol. 1, No. 2, 1987, pp. 107-113.

Nord et al., "Binding Proteins Selected from Combinatorial Libraries of an α-Helical Bacterial Receptor Domain", Nature Biotechnology, vol. 15, Aug. 1997, pp. 772-777.

O'Cuinn, "Peptide Metabolism in Cytoplasm of Brain Cell", Biochemical Society Transactions, vol. 26, No. 3, 1998, pp. 279-292.

Pace et al., "How to Measure and Predict the Molar Absorption Coefficient of a Protein", Protein Science, vol. 4, 1995, pp. 2411-2423.

Pall, "Protein A Ceramic HyperD F—Affinity Chromatography Sorbent", Product Note LPN PN702-004, 2004, pp. 1-6.

Palmer et al., "Design Of Stability at Extreme Alkaline pH in Streptococcal Protein G", Journal of Biotechnology vol. 134, 2008, pp. 222-230.

Patel et al., "Chemical Pathways of Peptide Degradation. II. Kinetics Of Deamidation of an Asparaginyl Residue in A Model Hexapeptide", Pharmaceutical Research, vol. 7, No. 7, 1990, pp. 703-711.

International Preliminary Report on Patentability received for PCT Application No. PCT/US2012/041070, dated Dec. 27, 2013, 13 pages.

International Search Report and Written Opinion received for PCT Application No. PCT/US2012/041070, dated Aug. 14, 2013, 7 pages.

Pearson et al., "Improved Tools for Biological Sequence Comparison", Proceedings of the National Academy of Sciences, vol. 85, No. 8, Apr. 1, 1988, pp. 2444-2448.

Popplewell et al., "Synthesis and Mutagenesis of an IgG-Binding Protein based upon Protein A of *Staphylococcus aureus*", Protein Engineering, vol. 4, No. 8, 1991, pp. 963-970.

Porath et al., "Group Fractionation of Plasma Proteins on Dipolar Ion Exchangers", Journal of Chromatography, vol. 51, 1970, pp. 479-489.

"UniProt Database Accession No. Q683L6", Retrieved from the Internet: URL: <http://www.uniprot.org/uniprot/Q683L6.txt>, Oct. 11, 2004, 1 page.

Robinson et al., "Controlled Deamidation of Peptides and Proteins: An Experimental Hazard and a Possible Biological Timer", Proceedings of the National Academy of Sciences, vol. 66, No. 3, Jul. 1970, pp. 753-757.

Robinson et al., "Rates of Nonenzymatic Deamidation of Glutaminyl and Asparaginyl Residues in Pentapeptides", Journal of the American Chemical Society, vol. 95, No. 24, Nov. 28, 1973, pp. 8156-8159.

Robinson et al., "Sequence Dependent Deamidation Rates for Model Peptides of Cytochrome C", Bonner Laboratory of Biology and Chemistry, University of California at San Diego, 1974, pp. 31-35.

Robinson et al., "Sequence Dependent Deamidation Rates for Model Peptides of Histone IV", Linus Pauling Institute of Science and Medicine, Menlo Park, 1974, pp. 279-282.

Roque et al., "Affinity-Based Methodologies and Ligands for Antibody Purification: Advances and Perspectives", Journal of Chromatography A, vol. 1160, 2007, pp. 44-55.

(56) References Cited

OTHER PUBLICATIONS

Saito et al., "High Level Expression of a Synthetic Gene Coding for IgC-Binding Domain B of Staphylococcal Protein A", Protein Engineering vol. 2, 1989, pp. 481-487.
Sambrook et al., "Molecular Cloning: A Laboratory Manual", Cold Spring Harbor Laboratory, Copyright 2012, 32 pages.
Scotchler et al., "Deamidation of Glutaminyl Residues: Dependence on pH, Temperature, and Ionic Strength", Analytical Biochemistry, vol. 59, No. 1, 1974, pp. 319-322.
Sjodahl, "Structural Studies on the Four Repetitive Fc-Binding Regions in Protein A from *Staphylococcus aureus*", European Journal of Biochemistry, vol. 78, No. 2, 1977, pp. 471-490.
Smith et al., "Comparison of Biosequences", Advances in Applied Mathematics, vol. 2, No. 4, 1981, pp. 482-489.
Starovasnik et al., "Antibody Variable Region Binding by Staphylococcal Protein A: Thermodynamic Analysis and Location of the Fv Binding Site On E-Domain", Protein Science, vol. 8, No. 7, Copyright 1999, pp. 1423-1431.
Ulhen et al., "Complete Sequence of the Staphylococcal Gene Encoding Protein A", A Gene Evolved Through Multiple Duplications, The Journal of Biological Chemistry, vol. 259, No. 3, 1984, pp. 1695-1702.
"Mabselect Sure—Studies on Ligand Toxicity, Leakage, Removal of Leached Ligand,and Sanitization", Process-scale Antibody Purification, Amersham Biosciences, 2004, pp. 1-6.
"Peptide Metabolism in Cytoplasm of Brain Cells", 665th Meeting, University of Southampton, Sep. 1, 1998, 1 page.
Extended European Search Report received for European Patent Application No. 012171045.3, dated Mar. 5, 2013, 19 pages.
Partial European Search Report received for European Patent Application No. 012171045.3, dated Sep. 24, 2012, 8 pages.
Extended European Search Report received for European Patent Application No. 09167670.0, dated Dec. 30, 2009, 7 pages.
Extended European Search Report received for European Patent Application No. 09180615.8, dated Sep. 16, 2010, 18 pages.
Notice of Opposition received for European Patent Application No. 09180615.8, dated Dec. 19, 2013, 24 pages.
Observation filed for the European application No. 09180615.8, on Jun. 3, 2014, 17 pages.
Partial European Search Report received for European Patent Application No. 09180615.8, dated May 20, 2010, 8 pages.
Extended European Search Report received for European Patent Application No. 12163614.6, dated Aug. 8, 2012, 8 pages.
Extended European Search Report received for European Patent Application No. 121636153, dated Aug. 8, 2012, 8 pages.
Extended European Search Report received for European Patent Application No. 12171108.9, dated Oct. 2, 2012, 16 pages.
Extended European Search Report received for European Patent Application No. 14163423.8, dated Oct. 7, 2014, 10 pages.
Yoshida et al., "Protein Having Affinity for Immunoglobulin, and Immunoglobulin-Binding Affinity Ligand", Unpublished Japanese Patent Application No. 2009-71766, filed on Mar. 24, 2009, Corresponds to U.S 20120208234 A1, 46 pages.
Altschul et al., "Basic Local Alignment Search Tool", Journal of Molecular Biology, vol. 215, 1990, pp. 403-410.
Amersham Biosciences, "RMP Protein A Sepharose Fast Flow", Data File, Affinity Chromatography, 2000, pp. 1-4.
Arshady, "Styrene Based Polymer Supports Developed by Suspension Polymerization", Chimica e L'Industria, vol. 70, No. 9, 1988, pp. 70-75.
Atkins et al., "S. Aureus IgG-Binding Proteins Spa and Sbi: Host Specificity and Mechanisms of Immune Complex Formation", Molecular Immunology, vol. 45, 2008, pp. 1600-1611.
Ausubel et al., "Current Protocols in Molecular Biology", Edited by Ausubel, John Wiley & Sons, 1988, 4410 pages.
Bowie et al., "Deciphering the Message in Protein Sequences: Tolerance to Amino Acid Substitutions", Science, vol. 247, Mar. 16, 1990, pp. 1306-1310.
Boyle et al., "Bacterial Fc Receptors", Nature Biotechnology, vol. 5, Jul. 1987, pp. 697-703.

Braisted et al., "Minimizing a Binding Domain from Protein A", Proc. Natl. Acad. Sci. USA, vol. 93, Jun. 1996, pp. 5688-5692.
Brown et al., "A Study of the Interactions Between an IgG-Binding Domain Based on the B Domain of Staphylococcal Protein A and Rabbit IgG", Molecular Biotechnology, vol. 10, 1998, pp. 9-16.
Brown et al., "Affinity Purification of Human IgG using Immobilised, Mutated Immunoglobulin-Binding Domains from Protein A of *Staphylococcus aureus*", Biochemical Society Transactions, vol. 26, 1998, 1 page.
Cedergren et al., "Mutational Analysis of the Interaction Between Staphylococcal Protein A and Human IgG", Protein Engineering, vol. 6, 1993, pp. 441-448.
Chen et al., "Immobilized Protein ZZ, an Affinity Tool for Immunoglobulin Isolation and Immunological Experimentation", Biotechnology and Applied Biochemistry, vol. 45, 2006, pp. 87-92.
Database WPI, "Week 200702", Thomson, AN 2007-012290, XP002683879, Sep. 26, 2012, 2 pages.
Deisenhofer, "Crystallographic Refinement and Atomic Models of a Human FC Fragment and its Complex with Fragment B of Protein A from *Staphylococcus aureus* at 2.9-and 2.8-Å Resolution", Biochemistry, vol. 20, No. 9, Apr. 28, 1981, pp. 2361-2370.
Flatmark et al., "Multiple Forms of Cytochrome C in the Rat", Precursor-Product Relationship Between The Main Component Cy I And The Minor Components Cy II and Cy III In Vivo, Apr. 10, 1968, pp. 1623-1629.
Flatmark, "On the Heterogeneity of Beef Heart Cytochrome C", Acta Chemica Scandinavica, vol. 18, 1964, pp. 1656-1666.
Füglistaller, "Comparison of Immunogloublin Binding Capacities and Ligand Leakage Using Eight Different Protein A Affinity Chromatography Matrices", Journal of Immunological Methods, vol. 124, 1989, pp. 171-177.
GE Healthcare, "Affinity Chromatography—Principles and Methods", Oct. 2007, pp. 28-37.
Geiger et al., "Deamidation, Isomerization, and Racemization at Asparaginyl and Aspartyl Residues in Peptides", Journal of Biological Chemistry, vol. 262, No. 2, Jan. 15, 1987, pp. 785-794.
Geneseq, "Inhibiting Complement Activation Comprises Contacting the System with a Complement-Binding Protein Comprising Sbi-III and/or Sbi-IV Domain Capable of Binding to C3 Protein", S. Aureus Spa Protein Inmunoglobulin-Binding Domain Spa-C, Apr. 17, 2008, 2 pages.
Ghose et al., "Antibody Variable Region Interactions with Protein A: Implications for the Development of Generic Purification Processes", Biotechnology and Bioengineering, vol. 92, No. 6, Dec. 20, 2005, pp. 665-673.
Ghose et al., "Protein A Affinity Chromatography for Capture and Purification of Monoclonal Antibodies and Fc-Fusion Proteins: Practical Considerations For Process Development", Process Scale Bioseparations for the Biopharmaceutical Industry, 2007, pp. 463-489.
Godfrey et al., "A Sensitive Enzyme-Linked Immunosorbent Assay (ELISA) for the Detection of Staphylococcal Protein A (Spa) Present as a Trace Contaminant of Murine Immunoglobulins Purified on Immobilized Protein A", Journal of Immunological Methods, vol. 149, 1992, pp. 21-27.
Graille et al., "Crystal Structure of a *Staphylococcus aureus* Protein A Domain Complexed with the Fab Fragment of a Human Igm Antibody: Structural Basis for Recognition of B-Cell Receptors and Superantigen Activity", Proceedings of the National Academy of Sciences, vol. 97, No. 10, May 9, 2000, pp. 5399-5404.
Gronberg et al., "Rapid Development of CIP Protocols for Affinity Media", GE Healthcare, 2008, 1 page.
Gulich et al., "Protein Engineering of an IgG-Binding Domain Allows Milder Elution Conditions During Affinity Chromatography", Journal of Biotechnology, vol. 76, No. 2-3, Jan. 21, 2000, pp. 233-243.
"UniProt Database Accession No. H3YRJ6", Retrieved from the Internet: URL: <http://www.uniprot.org/uniprot/H3YRJ6.txt>, Apr. 18, 2012, 1 page.
"Uniprot Database Accession No. H3Z2S0", Retrieved from the Internet: URL: <<http://www.uniprot.org/uniprot/H3Z2S0.txt>, Apr. 18, 2012, 1 page.

(56) References Cited

OTHER PUBLICATIONS

Hale et al., "Repeated Cleaning of Protein A Affinity Column with Sodium Hydroxide", Journal of Immunological Methods, vol. 171, 1994, pp. 15-21.

Henikoff et al., "Amino Acid Substitution Matrices from Protein Blocks", Proceedings of the National Academy of Sciences, vol. 89, Nov. 1992, pp. 10915-10919.

Hermanson et al., "Activation Methods", Chapter 2 Affinity Ligand Techniques, Academic Press, 1992, pp. 51-136.

Hjerten, "The Preparation of Agarose Spheres for Chromatography of Molecules and Particles", Biochimica et Biophysica Acta, vol. 79, No. 2, Mar. 30, 1964, pp. 393-398.

Hober et al., "Protein A Chromatography for Antibody Purification", Journal of Chromatography B, vol. 848 No. 1, Mar. 15, 2007, pp. 40-47.

Hulett et al., "The Second and Third Extracellular Domains of Fcγri (CD64) Confer the Unique High Affinity Binding of IgG2a", 1998, pp. 989-996.

Huston et al., "Multisite Association by Recombinant Proteins can Enhance Binding Selectivity", Biophysical Journal, vol. 62, 1992, pp. 87-91.

Jansson et al., "All Individual Domains of Staphylococcal Protein A Show Fab Binding", FEMS Immunology & Medical Microbiology vol. 20, No. 1, Jan. 1998, pp. 69-78.

Jendeberg et al. "Kinetic analysis of the interaction between protein A domain variants and human Fc using plasmon resonance detection" Journal of Molecular Recognition, 1995, vol. 8, No. 4, pp. 270-278.

\* cited by examiner

Figure 1

DNA Sequences of the wt IgG binding domains of Protein A

SEQ ID NO:1- E domain DNA sequence
GCGCAACAAAACGCTTTCTATCAGGTACTGAACATGCCTAACCTGAACGCCGATCAG
CGTAACGGCTTCATCCAAAGCCTGAAGGACGACCCGAGCCAGTCCGCAAACGTTCTG
GGTGAAGCTCAAAAACTGAACGACAGCCAGGCACCGAAAGCTGAC SEQ ID NO:2- D domain DNA sequence
GCCCAACAGAACAAATTTAACAAAGACCAGCAGTCCGCGTTCTACGAGATTCTGAAC
ATGCCTAACCTGAATGAAGAACAGCGCAACGGTTTTATTCAGTCTCTGAAGGACGAT
CCTTCTCAATCCACCAACGTACTGGGCGAAGCGAAGAAACTGAACGAATCTCAGGCT
CCGAAG SEQ ID NO:3- A domain DNA sequence
GCCGACAACAACTTCAACAAAGAGCAGCAAAACGCTTTCTACGAAATCCTGAATATG
CCAAATCTGAACGAAGAGCAGCGTAACGGTTTCATCCAATCTCTGAAAGACGATCCG
TCCCAGTCCGCGAATCTGCTGGCGGAGGCTAAAAAGCTGAACGAATCCCAGGCTCCG
AAA SEQ ID NO:4- B domain DNA sequence
GCAGACAATAAGTTCAATAAAGAGCAGCAGAACGCATTTTACGAGATCCTGCATCTG
CCGAACCTGAACGAAGAACAACGCAACGGTTTCATTCAGAGCCTGAAAGACGACCCA
TCTCAGTCCGCTAACCTGCTGGCGGAAGCAAAGAAGCTGAACGATGCACAGGCGCCG
AAA SEQ ID NO:5- C domain DNA sequence
GCGGATAACAAATTCAACAAGGAGCAACAGAACGCATTCTATGAAATTCTGCACCTG
CCGAATCTGACGGAGGAGCAACGTAACGGCTTTATCCAGTCCCTGAAGGATGATCCG
TCTGTGTCTAAAGAGATCCTGGCGGAGGCAAAAAAACTGAATGATGCACAAGCTCCG
AAA

Figure 2

SEQ ID NO:6- Z domain DNA sequence
GTAGACAACAAATTCAATAAAGAACAGCAGAACGCTTTCTATGAAATCCTGCACCTG
CCGAACCTGAACGAAGAACAGCGTAACGCGTTTATCCAGTCCCTGAAAGACGACCCG
AGCCAGAGCGCAAATCTGCTGGCCGAAGCGAAAAAGCTGAACGATGCCCAGGCGCCG
AAA

Figure 3

IgG binding domain sequence alignment

```
B   --------AQQNAFYQVLNMPNLNAAQRNGFIQSLKDDPSQSANVLGEAQKLNDSQAPK  51  (SEQ ID NO:7)
D   ADAQQNNFNKDQQSAFYEILNMPNLNEAQRNGFIQSLKDDPSQSTKVLGEAKKLNDAQAPK  61  (SEQ ID NO:8)
A   --ADNN-FNKEQQNAFYEILNMPNLNEEQRNGFIQSLKDDPSQSANLLAEAKKLNESQAPK  58  (SEQ ID NO:9)
B   ---ADNKFNKEQQNAFYEILHLPNLNEEQRNAFIQSLKDDPSQSAMLLAEAKKLNDAQAPK  58  (SEQ ID NO:10)
C   ---ADNKFNKEQQNAFYEILHLPNLNEEQRNGFIQSLKDDPSVSKEILAEAKKLNDAQAPK  58  (SEQ ID NO:11)
             :* ***::::* *** ****:***:************. *:****:***:.****
```

Figure 4

SEQ ID NO:12- Z domain amino acid sequence
VDNKFNKEQQ NAFYEILHLP NLNEEQRNAF IQSLKDDPSQ SANLLAEAKKL
NDAQAPK

FIG. 6

Wildtype B domain 6Histidine (SEQ ID NO: 13)
MADNKFNKEQQNAFYEILHLPNLNEEQRNGFIQSLKDDPSQSANLLAEAKKL
NDAQAPKHHHHHH E24M (SEQ ID NO: 14)
MADNKFNKEQQNAFYEILHLPNLNMEQRNGFIQSLKDDPSQSANLLAEAKKL
NDAQAPKHHHHHH E24I (SEQ ID NO: 15)
MADNKFNKEQQNAFYEILHLPNLNIEQRNGFIQSLKDDPSQSANLLAEAKKL
NDAQAPKHHHHHH E24F (SEQ ID NO: 16)
MADNKFNKEQQNAFYEILHLPNLNFEQRNGFIQSLKDDPSQSANLLAEAKKL
NDAQAPKHHHHHH E24T (SEQ ID NO: 17)
MADNKFNKEQQNAFYEILHLPNLNTEQRNGFIQSLKDDPSQSANLLAEAKKL
NDAQAPKHHHHHH E24P (SEQ ID NO: 18)
MADNKFNKEQQNAFYEILHLPNLNPEQRNGFIQSLKDDPSQSANLLAEAKKL
NDAQAPKHHHHHH E24W (SEQ ID NO: 19)
MADNKFNKEQQNAFYEILHLPNLNWEQRNGFIQSLKDDPSQSANLLAEAKKL
NDAQAPKHHHHHH E24R (SEQ ID NO: 20)
MADNKFNKEQQNAFYEILHLPNLNREQRNGFIQSLKDDPSQSANLLAEAKKL
NDAQAPKHHHHHH E24V (SEQ ID NO: 21)
MADNKFNKEQQNAFYEILHLPNLNVEQRNGFIQSLKDDPSQSANLLAEAKKL
NDAQAPKHHHHHH E24L (SEQ ID NO: 22)
MADNKFNKEQQNAFYEILHLPNLNLEQRNGFIQSLKDDPSQSANLLAEAKKL
NDAQAPKHHHHHH

FIG. 6 Cont'd

E24Y (SEQ ID NO: 23)
MADNKFNKEQQNAFYEILHLPNLNYEQRNGFIQSLKDDPSQSANLLAEAKKL
NDAQAPKHHHHHH

E24H (SEQ ID NO: 24)
MADNKFNKEQQNAFYEILHLPNLNHEQRNGFIQSLKDDPSQSANLLAEAKKL
NDAQAPKHHHHHH

E24K (SEQ ID NO: 25)
MADNKFNKEQQNAFYEILHLPNLNKEQRNGFIQSLKDDPSQSANLLAEAKKL
NDAQAPKHHHHHH

E24D (SEQ ID NO: 26)
MADNKFNKEQQNAFYEILHLPNLNDEQRNGFIQSLKDDPSQSANLLAEAKKL
NDAQAPKHHHHHH

FIG. 7

Wildtype B domain 6 Histidine (SEQ ID NO: 27)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGCTGGCCGAAGCAAAGAAGCTGAACGATGCACAGGCGCCGAAACATCATCACCATCA
CCACTAATAAGGATCC E24M (SEQ ID NO: 28)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGATGGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24I (SEQ ID NO: 29)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGATTGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24F (SEQ ID NO: 30)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGTTTGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24T (SEQ ID NO: 31)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGACCGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24P (SEQ ID NO: 32)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGCCGGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24N (SEQ ID NO: 33)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGAACGAAGAACAACGCAACGGTTTCATTCAGAGCCTGAAAGACGACCCATCTCA
GTCCGCTAACCTGCTGGCCGAAGCAAAGAAGCTGAACGATGCACAGGCGCCGAAACATCATCACCATCA
CCACTAATAAGGATCC E24R (SEQ ID NO: 34)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGCGTGAAGAACAACGCAACGGTTTCATTCAGAGCCTGAAAGACGACCCATCTCA
GTCCGC

FIG. 7 Cont'd

TAACCTGCTGGCGGAAGCAAAGAAGCTGAACGATGCACAGGCGCCGAAACATCATCACCATCACCACTA
ATAAGGATCC

E24V (SEQ ID NO: 35)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTG????GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

E24L (SEQ ID NO: 36)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTG????GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

E24Y (SEQ ID NO: 37)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTG????GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

E24R (SEQ ID NO: 38)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTG????GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

E24K (SEQ ID NO: 39)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTGA??GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

E24D (SEQ ID NO: 40)
GAATTCTAATACGACTCACTATAACGCGTCCACAACGGTTTCCCTCTAGAAATAATTTTGTTTAACTTT
AAGAAGGAGATATACATATGGCAGACAATAAGTTCAATAAAGAGCAGCAGAACGCATTTTACGAGATCC
TGCTCTGCCGAACCTG????GAAGAACAACGCAACGGTTTCATTCAGAGCCTGAAAGACGACCCATCTCA
GTCCGCTAACCTGCTGGCGGAAGCAAAGAAGCTGAACGATGCACAGGCGCCGAAACATCATCACCATCA
CCACTAATAAGGATCC

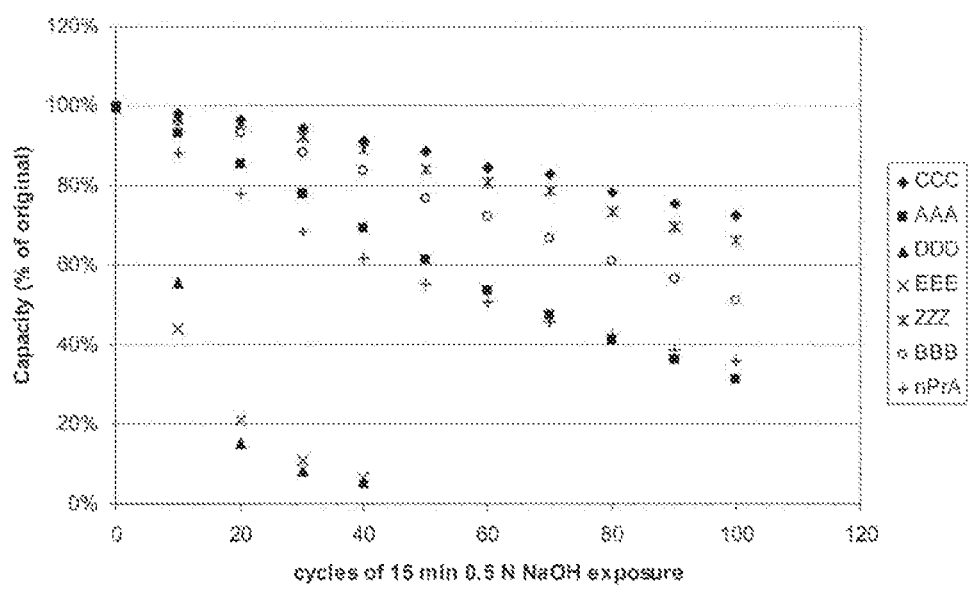

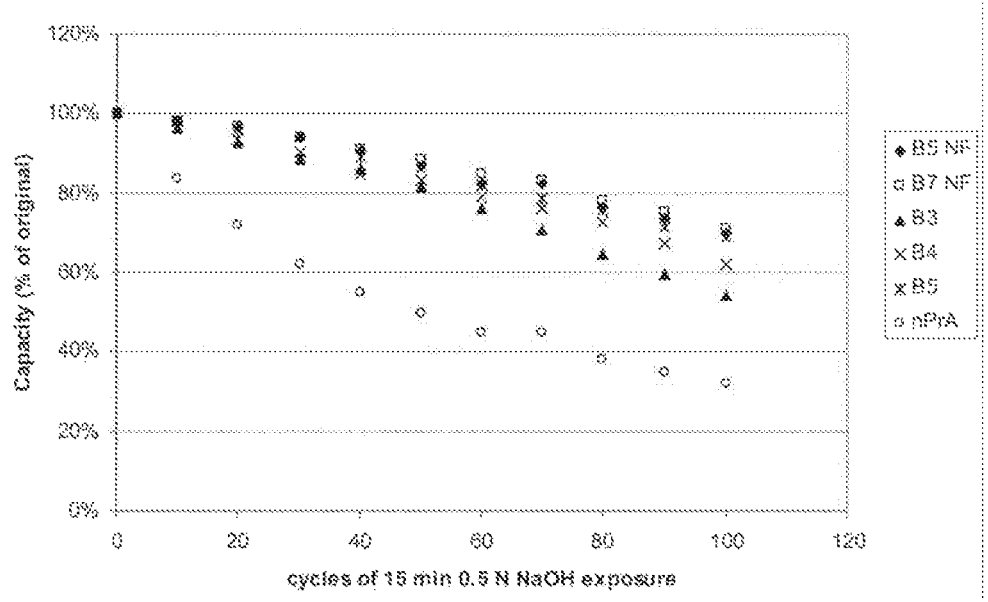

CAUSTIC STABLE CHROMATOGRAPHY LIGANDS

RELATED APPLICATIONS

The present application is a continuation of U.S. application Ser. No. 12/653,888, filing date Dec. 18, 2009, which claims the benefit of U.S. Provisional Patent Application No. 61/203,664, filing date Dec. 24, 2008, the entire content of each of which is incorporated herein in its entirety.

SEQUENCE LISTING

The instant application contains a Sequence Listing which has been submitted electronically in ASCII format and is hereby incorporated by reference in its entirety. Said ASCII copy, created on Aug. 15, 2018, is named MCA-1032-1 US SL.txt and is 24,945 bytes in size.

FIELD OF THE INVENTION

The present invention relates to chromatography ligands having improved caustic stability, e.g., ligands based on immunoglobulin-binding proteins such as, Staphylococcal protein A, as well as chromatography matrices comprising such ligands.

BACKGROUND

Ligands used in affinity chromatography typically confer a high selectivity for the target molecule, thereby resulting in high yield and fast and economical purification of target molecules. Staphylococcal protein A (SpA) based reagents and chromatography matrices have found a widespread use in the field of affinity chromatography for capture and purification of antibodies as well as in antibody detection methods due to its ability to bind IgG without significantly affecting the affinity of the immunoglobulin for antigen.

Accordingly, various reagents and media comprising protein A-ligands have been developed and are commercially available including, for example, ProSep®-vA High Capacity, ProSep® vA Ultra and ProSep® UltraPlus (Millipore) and Protein A Sepharose™, MabSelect™, MabSelect Xtra™ and MabSelect SuRe® (GE Healthcare) and Poros MabCapture A™ (Applied Biosystems).

In order to maintain selectivity and binding capacity of the chromatography ligands including, e.g., resins including SpA based chromatography ligands, the ligand bound resins, referred to as chromatography matrices, have to be cleaned and are typically cleaned under alkaline conditions, e.g., with sodium hydroxide. For example, a standard process which is used for cleaning and restoring the matrix is a cleaning-in-place (CIP) alkaline protocol, which typically involves treatment of the matrix with 1M NaOH, pH 14. However, such harsh treatment is often undesirable, especially, where the ligand is a protein or a protein-based molecule.

SUMMARY OF THE INVENTION

The present invention provides alkaline-stable SpA-based chromatography ligands which, for example, are capable of withstanding repeated cleaning-in-place (CIP) cycles. More specifically, ligands according to the invention are able to withstand conventional alkaline cleaning for a prolonged period of time, which renders the ligands attractive candidates, especially for cost-effective large-scale purification of immunoglobulins.

In one aspect of the present invention, an alkaline-stable chromatography ligand comprises two or more domains of SpA. For example, in some embodiments according to this aspect, an alkaline-stable chromatography ligand is provided, which comprises two or more B domains or two or more Z domains of Staphylococcus protein A (SpA), or a functional fragment or variant thereof, where the two or more B domains or two or more Z domains are attached to a chromatography resin at more than one site on the resin.

In some embodiments according to this aspect, the ligand comprises three or more B domains or three or more Z domains of SpA, or a functional fragment or variant thereof, where the three or more B domains or three or more Z domains are attached to a chromatography resin at more than one site on the resin. In some other embodiments, the ligand comprises four or more B domains or four or more Z domains of SpA, where the four or more B domains or four or more Z domains are attached to a chromatography resin at more than one site on the resin. In yet other embodiments, the ligand comprises five or more B domains or five or more Z domains of SpA; or six or more B domains or six or more Z domains of SpA; or seven or more B domains or seven or more Z domains of SpA, where the five or more B domains, or five or more Z domains, or six or more B domains, or six or more Z domains, or seven or more B domains or seven or more Z domains are attached to a chromatography resin at more than one site on the resin.

In another aspect according to the present invention, an alkaline-stable chromatography ligand comprises one or more isolated E, D, A, B, C or Z domains of Staphyloccocus protein A, where the one or more isolated domains comprise one or more amino acid residues at position n+1 mutated to any naturally occurring amino acid except cysteine (C), serine (S), alanine (A), glycine (G), asparagine (N), or glutamine (Q). In some embodiments, n represents the asparagine residue at position 23 of an isolated SpA domain. Exemplary ligands having a mutation at position 24 of an isolated SpA domain where n represents an asparagine are shown in Table I.

TABLE I

| SpA domains including modifications | Designation |
|---|---|
| E, D, A, B, C or Z domain-glutamic acid 24 or aspartic acid 24 replaced with methionine | E-D24M |
| | D-E24M |
| | A-E24M |
| | B-E24M |
| | C-E24M |
| | Z-E24M |
| E, D, A, B, C or Z domain-glutamic acid 24 or aspartic acid 24 replaced with isoleucine | E-D24I |
| | D-E24I |
| | A-E24I |
| | B-E24I |
| | C-E24I |
| | Z-E24I |
| E, D, A, B, C or Z domain-glutamic acid 24 or aspartic acid 24 replaced with phenylalanine | E-D24F |
| | D-E24F |
| | A-E24F |
| | B-E24F |
| | C-E24F |
| | Z-E24F |
| E, D, A, B, C or Z domain-glutamic acid 24 or aspartic acid 24 replaced with threonine | E-D24T |
| | D-E24T |
| | A-E24T |
| | B-E24T |
| | C-E24T |
| | Z-E24T |

TABLE I-continued

| SpA domains including modifications | Designation |
|---|---|
| E, D, A, B, C or Z domain-glutamic acid 24 or aspartic acid 24 replaced with proline | E-D24P |
| | D-E24P |
| | A-E24P |
| | B-E24P |
| | C-E24P |
| | Z-E24P |
| E, D, A, B, C or Z domain-glutamic acid 24 or aspartic acid 24 replaced with tryptophan | E-D24W |
| | D-E24W |
| | A-E24W |
| | B-E24W |
| | C-E24W |
| | Z-E24W |
| E, D, A, B, C or Z domain-glutamic acid 24 or aspartic acid 24 replaced with arginine | E-D24R |
| | D-E24R |
| | A-E24R |
| | B-E24R |
| | C-E24R |
| | Z-E24R |
| E, D, A, B, C or Z domain-glutamic acid 24 or aspartic acid 24 replaced with valine | E-D24V |
| | D-E24V |
| | A-E24V |
| | B-E24V |
| | C-E24V |
| | Z-E24V |
| E, D, A, B, C or Z domain-glutamic acid 24 or aspartic acid 24 replaced with leucine | E-D24L |
| | D-E24L |
| | A-E24L |
| | B-E24L |
| | C-E24L |
| | Z-E24L |
| E, D, A, B, C or Z domain-glutamic acid 24 or aspartic acid 24 replaced with tyrosine | E-D24Y |
| | D-E24Y |
| | A-E24Y |
| | B-E24Y |
| | C-E24Y |
| | Z-E24Y |
| E, D, A, B, C or Z domain-glutamic acid 24 or aspartic acid 24 replaced with histidine | E-D24H |
| | D-E24H |
| | A-E24H |
| | B-E24H |
| | C-E24H |
| | Z-E24H |
| E, D, A, B, C or Z domain-glutamic acid 24 or aspartic acid 24 replaced with lysine | E-D24K |
| | D-E24K |
| | A-E24K |
| | B-E24K |
| | C-E24K |
| | Z-E24K |
| E, D, A, B, C or Z domain-glutamic acid 24 or aspartic acid 24 replaced with glutamic acid | D-E24D |
| | A-E24D |
| | B-E24D |
| | C-E24D |
| | Z-E24D |

The single letter codes for the naturally occurring amino acids as well as the corresponding three letter codons encoding for each amino acid are depicted in Table II. In general, due to the degeneracy of the codon, more than one three letter codon can encode for the same amino acid.

TABLE II

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC Cys (C) |
| | TTA Leu (L) | TCA Ser (S) | TAA Stop | TGA stop |
| | TTG Leu (L) | TCG Ser (S) | TAG Stop | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Also encompassed by the present invention is a chromatography matrix comprising a ligand according to one or more aspects of the invention coupled to a solid support such as, e.g., at least one insoluble carrier.

Additionally, provided herein are methods of using the ligands described herein. Accordingly, a method of affinity purifying one or more target molecules (e.g., immunoglobulins) from a sample is provided, where the method comprising the steps of: (a) providing a sample comprising one or more target molecules (e.g., immunoglobulins); (b) contacting the sample with a matrix according to the invention under conditions such that the one or more target molecules (e.g., immunoglobulins) bind to the matrix; and (c) recovering the one or more bound target molecules (e.g., immunoglobulins) by eluting under suitable conditions such as, for example, a suitable pH.

In some embodiments, an alkaline-stable chromatography ligand according to the present invention retains at least 95% of its binding capacity after 5 hours, or after 10 hours, after 15 hours, or after 20 hours, or after 25 hours, or after 30 hours of incubation in 0.5 M NaOH.

The immunoglobulins which are capable of being bound by the various ligands described herein include, e.g., IgG, IgA and IgM, or any fusion protein comprising antibody and any fragment of antibody.

Also provided herein are nucleic acid molecules encoding the various ligands described herein, as well as host cells including such nucleic acid molecules. In some embodiments, a host cell is a prokaryotic cell. In other embodiments, a host cell is a eukaryotic cell.

Additionally, the present invention encompasses a library of polypeptides comprising one or more ligands described herein, and functional fragments and variants thereof. In yet another embodiment, the present invention provides a library of nucleic acid molecules encoding one or more ligands encompassed by the present invention or encoding functional fragments and variants thereof.

In some embodiments, the present invention provides SpA based ligands which exhibit altered (increased or decreased) binding to a Fab portion of an immunoglobulin compared to the previously known SpA ligands, while retaining the ability to bind the Fc portion of the immunoglobulin. In one embodiment, an SpA based ligand according to the present invention exhibits decreased binding to a Fab portion of an immunoglobulin compared to wild type SpA. In an exemplary embodiment, an alkaline-stable chromatography ligand according to the present invention further includes the amino acid glycine at position 29 replaced with an alanine. In another embodiment, an alkaline stable chromatography ligand according to the present invention further includes the glycine at position 29 replaced with an amino acid other than alanine or tryptophan.

BRIEF DESCRIPTION OF THE DRAWINGS

FIG. 1 depicts the nucleic acid sequences for the wild type (wt) IgG binding domains of SpA, represented by SEQ ID NOs:1-5. SEQ ID NO:1 represents the nucleic acid sequence for the wt E domain; SEQ ID NO: 2 represents the nucleic acid sequence for the wt D domain; SEQ ID NO: 3 represents the nucleic acid sequence for the wt A domain; SEQ ID NO: 4 represents the nucleic acid sequence for the wt B domain; and SEQ ID NO: 5 represents the nucleic acid sequence for the wt C domain.

FIG. 2 depicts the nucleic acid sequence for the Z domain of SpA, represented by SEQ ID NO: 6.

FIG. 3 depicts the amino acid sequence alignments of the wild type (wt) IgG binding domains of SpA (E, D, A, B and C). SEQ ID NO: 7 represents the amino acid sequence of the wt E domain; SEQ ID NO: 8 represents the amino acid sequence of the wt D domain; SEQ ID NO: 9 represents the amino acid sequence of the wt A domain; SEQ ID NO: 10 represents the amino acid sequence of the wt B domain; and SEQ ID NO: 11 represents the amino acid sequence of the wt C domain.

FIG. 4 depicts the amino acid sequence of the Z domain, represented by SEQ ID NO: 12.

FIG. 6 depicts the amino acid sequences for the his-tagged wt B domain of SpA as well as the various his-tagged n+1 mutants. SEQ ID NO: 13 represents the amino acid sequence for the his-tagged wt B domain of SpA and SEQ ID NOs: 14, 15, 16, 17, 18, 19, 20, 21, 22, 23, 24, 25 and 26 represent the amino acid sequences for the n+1 B domain mutants E24M, E24I, E24F, E24T, E24P, E24W, E24R, E24V, E24L, E24Y, E24H, E24K and E24D, respectively. The sequence of the His6 tag is disclosed in SEQ ID NO:42.

FIG. 7 depicts the nucleic acid sequences for the his-tagged wt B domain of SpA as well as nucleic acid sequences encoding the various his-tagged n+1 mutants. SEQ ID NO: 27 represents the nucleic acid sequence encoding the his-tagged wt B domain of SpA and SEQ ID NOs: 28, 29, 30, 31, 32, 33, 34, 35, 36, 37, 38, 39 and 40 represent the nucleic acid sequences encoding the n+1 B domain mutants E24M, E24I, E24F, E24T, E24P, E24W, E24R, E24V, E24L, E24Y, E24H, E24K and E24D, respectively. The sequence of the His6 tag is disclosed in SEQ ID NO:42.

FIG. 9 depicts the results of an exemplary experiment to assay for the percent retained IgG binding capacity of the various SpA domain trimers (i.e., EEE, DDD, AAA, BBB, CCC and ZZZ) subsequent to their multipoint attachment to an agarose resin. nPrA refers to the wt SpA. The X-axis represents the number of cycles of caustic exposure, where each cycle consists of a 15 minute exposure to 0.5 N NaOH. The Y-axis represents the retained IgG binding capacity of the attached SpA ligands. As shown in the graph in FIG. 9, the ligands including C or Z domain trimers are roughly equivalent in their caustic stability and are more caustic stable than the ligands including B domain trimers, which are more caustic stable than the ligands including A domain trimers, which are more caustic stable than the ligands including E or D domain trimers.

FIG. 10 depicts the results of an exemplary experiment to assay for the percent retained IgG binding capacity of attached ligands according to the invention, containing three (B3), or four (B4), or five (B5) B domains, attached via multipoint attachment to an agarose resin. Also, attached ligands containing five B domains or seven B domains and additionally including a mutation to reduce Fab binding (G29A) are used, referred to as B5-NF and B7-NF, respectively. nPrA refers to the wt SpA. The X-axis represents the number of cycles of caustic exposure, where each cycle consists of a 15 minute exposure to 0.5 N NaOH. The Y-axis represents the retained IgG binding capacity of the attached SpA ligands. As shown in the graph in FIG. 10, the level or extent of caustic stability is directly proportional to the number of B domains in the ligands and is not altered by the G29A mutation to decrease Fab binding.

DETAILED DESCRIPTION OF THE INVENTION

Figure 5:
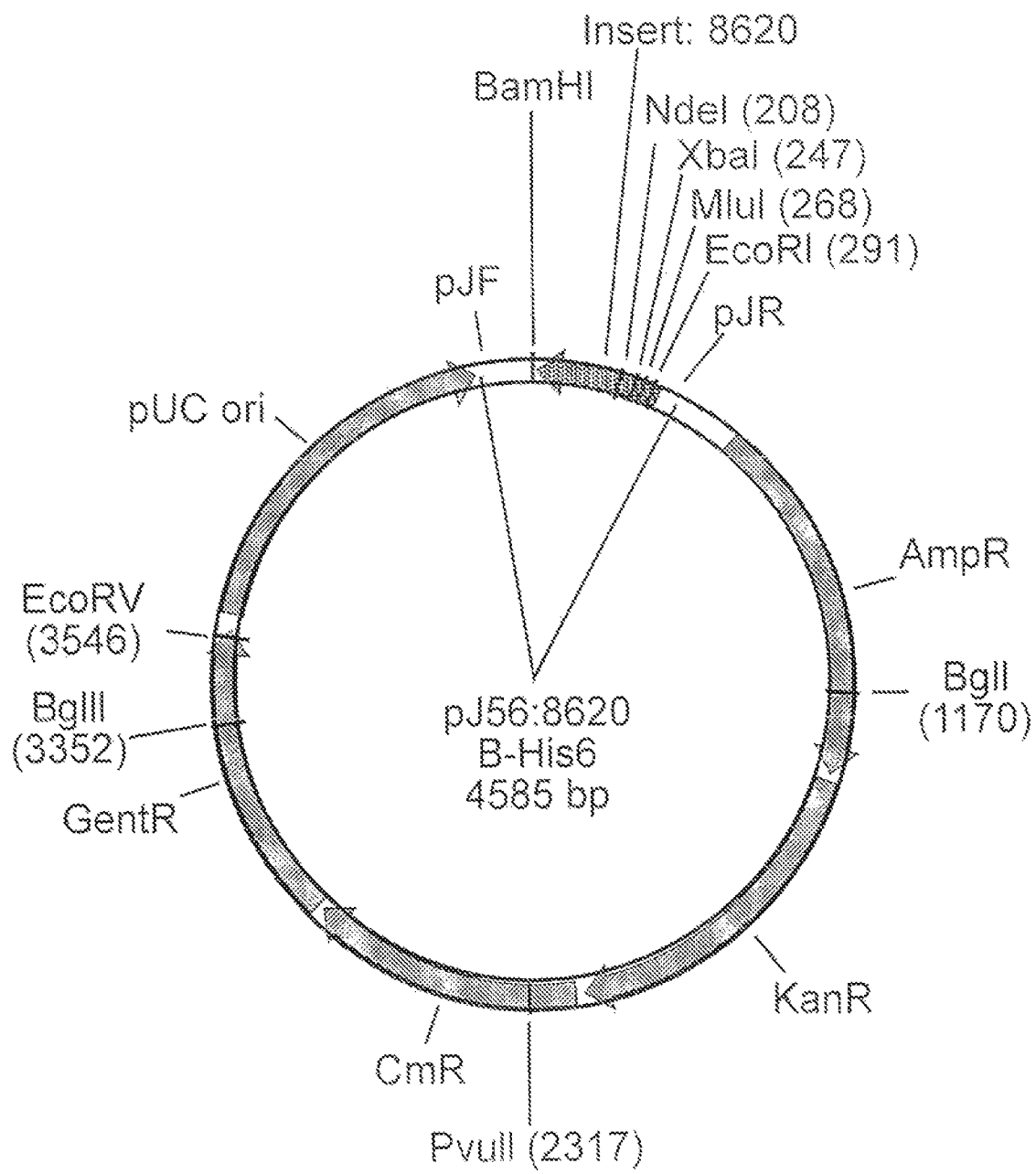
FIG. 5 depicts a schematic of the plasmid pJ56:8620. The sequence of the His6 tag is disclosed in SEQ ID NO:42.

The present invention provides SpA based alkaline-stable chromatography ligands, and in particular, ligands based on one or more domains of SpA. Previously described exemplary SpA based alkaline-stable chromatography ligands include, for example, those described in International PCT patent application no. WO2008/039141, which discusses alkaline-stable chromatography ligands based on the C domain of SpA which are capable of binding the Fab portions of antibodies and are coupled to an insoluble carrier at a single site using a terminal coupling group; and those described in U.S. Pat. No. 6,831,161, which discusses SpA based alkaline based chromatography ligands where one or more asparagine amino acid residues have modified.

In order that the present disclosure may be more readily understood, certain terms are first defined. Additional definitions are set forth throughout the detailed description.

Definitions

As used herein, the term "SpA" or "protein A of *Staphylococcus aureus*," refers to a 42Kda multi-domain protein isolated from the bacterium *Staphylococcus aureus*. SpA is bound to the bacterial cell wall via its carboxy-terminal cell wall binding region, referred to as the X domain. At the amino-terminal region, it includes five immunoglobulin-binding domains, referred to as E, D, A, B, and C (Sjodhal, *Eur J Biochem*. September 78(2):471-90 (1977); Uhlen et al., *J Biol Chem*. February 259(3):1695-702 (1984). Each of these domains contains approximately 58 amino acid residues, and they share 65-90% amino acid sequence identity. The Z domain of SpA is an engineered analogue of the B domain of SpA and includes an alanine instead of a glycine residue at position 29 (Nilsson, et al., *Protein engineering*, Vol. 1, No. 2, 107-113, 1987.). Each of the E, D, A, B and C domains of SpA possess distinct Ig-binding sites. One site is for Fcγ (the constant region of IgG class of Ig) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

The cloning of the gene encoding SpA is described in U.S. Pat. No. 5,151,350, the entire contents of which are incorporated by reference herein in their entirety.

The present invention provides SpA-based alkaline-stable chromatography ligands. In some aspects according to the present invention, an alkaline stable chromatography ligand comprises two or more, or three or more, or four or more, or five or more, or six or more, or seven or more of isolated wt B or Z domain of SpA. In other aspects according to the present invention, an alkaline stable chromatography ligand comprises one or more isolated E, D, A, B, C or Z domains of SpA, where the one or more isolated domains comprise one or more amino acid residues at position n+1 mutated to an amino acid selected from the group consisting of tryptophan, arginine, threonine, isoleucine, valine and methionine, wherein n represents an asparagine.

In a particular embodiment, the present invention provides a chromatography ligand comprising two or more B domains of SpA, attached to a chromatography resin at more than one site on the resin. In another embodiment, the present invention provides a chromatography ligand comprising two or more Z domains of SpA, attached to a chromatography resin at more than one site on the resin. In yet another embodiment, a chromatography ligand comprises two or more C domains of SpA, attached to a chromatography resin at more than one site on the resin.

Also encompassed by the present invention are amino acid variants of SpA, which may differ from the parent amino acid sequence from which they are derived, in the substitution, deletion and/or insertion of one or more amino acids anywhere within the parent amino acid sequence and are alkaline stable. In some embodiments, amino acid sequence variants will possess at least about 70%, or at least about 80%, or at least about 85%, or at least about 90%, or at least about 95%, or at least about 96%, or at least about 97%, or at least about 98% identity with the parent sequence (i.e. wt SpA domains or Z domain), where such variants are alkaline stable. In a particular embodiment, variants of SpA further include the glycine amino acid residue at position 29 replaced by an amino acid residue other than alanine or tryptophan, while retaining its alkaline stability.

The term "functional variant" of a protein means herein a variant protein, where the function, in relation to the invention defined as alkaline stability, is essentially retained. Functional variants include, and are not limited to, SpA variants including more than domain of SpA, e.g., dimers, trimers, multimers of various domains of SpA and SpA variants having a deletion, substitution and/or addition of one or more amino acids in one or more wild type domains of SpA, while retaining the alkaline stability, as defined herein.

The term "parental molecule" is used herein for the corresponding protein in the form before it is modified according to the invention or a mutation according to the invention has been introduced.

The term "sequence identity" means that two nucleotide or amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As used interchangeably herein, the terms "E domain," "E domain of SpA," and "E domain of *Staphylococcus* protein A," refer to the polypeptide whose amino acid sequence is set forth in SEQ ID NO:7 or that encoded by, e.g., the nucleotide sequence set forth in SEQ ID NO: 1. The "E domain" is a 51 amino acid polypeptide that folds into a three-helix bundle structure. It is capable of binding Fc via residues on the surface of helices 1 and 2, or to Fab via residues on the surface of helices 2 and 3. In some embodiments, an E domain according to the invention is at least 70% identical, or at least 80% identical, or at least 90% identical or at least 95% or more identical in sequence to the amino acid sequence set forth in SEQ ID NO:7.

As used interchangeably herein, the terms "D domain," "D domain of SpA," and "D domain of *Staphylococcus* protein A," refer to the polypeptide whose amino acid sequence is set forth in SEQ ID NO: 8 or that encoded by e.g., the nucleotide sequence set forth in SEQ ID NO: 2. The "D domain" is a 61 amino acid polypeptide that folds into a three-helix bundle structure. It is capable of Fc binding via residues on the surface of helices 1 and 2, or to Fab via residues on the surface of helices 2 and 3. In some embodiments, a D domain according to the invention is at least 70% identical, or at least 80% identical, or at least 90% identical or at least 95% or more identical in sequence to the amino acid sequence set forth in SEQ ID NO: 8.

As used interchangeably herein, the terms "A domain," "A domain of SpA," and "A domain of *Staphylococcus* protein A," refer to the polypeptide whose amino acid sequence is set forth in SEQ ID NO: 3 or that encoded by, e.g., the nucleotide sequence set forth in SEQ ID NO: 9. The "A domain" is a 58 amino acid polypeptide that folds into a three-helix bundle structure. It is capable of Fc binding via residues on the surface of helices 1 and 2, or to Fab via residues on the surface of helices 2 and 3. In some embodiments, an A domain according to the invention is at least 70% identical, or at least 80% identical, or at least 90% identical or at least 95% or more identical in sequence to the amino acid sequence set forth in SEQ ID NO: 3.

As used interchangeably herein, the terms "B domain," "B domain of SpA," and "B domain of *Staphylococcus* protein A," refer to the polypeptide whose amino acid sequence is set forth in SEQ ID NO: 10 or that encoded by, e.g., the nucleotide sequence set forth in SEQ ID NO: 4. The "B domain" is a 58 amino acid polypeptide that folds into a three-helix bundle structure. It is capable of Fc binding via residues on the surface of helices 1 and 2, or to Fab via residues on the surface of helices 2 and 3. In some embodiments, a B domain according to the invention is at least 70% identical, or at least 80% identical, or at least 90% identical or at least 95% or more identical in sequence to the amino acid sequence set forth in SEQ ID NO: 10.

As used interchangeably herein, the terms "C domain," "C domain of SpA," and "C domain of *Staphylococcus* protein A," refer to the polypeptide whose amino acid sequence is set forth in SEQ ID NO: 11 or that encoded by, e.g., the nucleotide sequence set forth in SEQ ID NO: 5. The "C domain" is a 58 amino acid polypeptide that folds into a three-helix bundle structure. It is capable of Fc binding via residues on the surface of helices 1 and 2, or to Fab via residues on the surface of helices 2 and 3. In some embodiments, a C domain according to the invention is at least 70% identical, or at least 80% identical, or at least 90% identical or at least 95% or more identical in sequence to the amino acid sequence set forth in SEQ ID NO: 11.

As used interchangeably herein, the terms "Z domain," "Z domain of SpA" and "Z domain of protein A," refer to the three helix, 59 amino acid polypeptide that is a variant of the B domain of protein A. The amino acid sequence of the Z domain is set forth in SEQ ID NO: 12. An exemplary Z domain is described in Nilsson et al., *Protein Engng.*, 1:107-113 (1997), the entire contents of which are incorporated by reference herein.

The term "alkaline-stable," "alkaline stability," "caustic stable" or "caustic stability," as used herein, generally refers to the ability of a chromatography ligand according to the present invention, either alone or when immobilized onto a chromatography resin, to withstand repeated cleaning-in-place (CIP) cycles using alkaline wash without losing its binding capacity. In general, it is assumed that a resin, by itself, onto which a ligand according to the invention is immobilized, contributes to less than a 5% change in stability after having been soaked in 0.5 M NaOH for up to 30 hours. For example, in some embodiments, chromatography ligands according to the invention are able to withstand conventional alkaline cleaning for a prolonged period of time, which renders the ligands attractive candidates, especially for cost-effective large-scale purification of immunoglobulins. In some embodiments, a ligand according to the present invention exhibits an improved chemical stability in an alkaline environment, which may be defined, for example, as that having an increased pH value such as above about 10, or up to about 13 or 14. Alternatively, the alkaline environment can be defined by the concentration of a base, e.g., about 1.0 M NaOH, or about 0.7 M NaOH, or about 0.5 M NaOH. In one embodiment, alkaline stability refers to the ability of an alkaline-stable chromatography ligand according to the present invention to retain at least 80%, or at least 85%, or at least 90%, or at least 95% of its binding capacity after 5 hours, or after 10 hours, after 15 hours, or after 20 hours, or after 25 hours, or after 30 hours of incubation in 0.5 M NaOH. In another embodiment, alkaline stability refers to a decrease in the binding capacity of the ligand by less than 70%, or less than 60%, or less than 50%, or less than 30% even after treatment with 0.5 M NaOH for 5 hours or 7.5 hours or 10 hours or 15 hours or 20 hours or 25 hours or 30 hours.

In some embodiments, SpA based chromatography ligands according to the present invention exhibit an increased or improved alkaline stability as compared to wild type SpA.

Alkaline stability can be readily measured by one of ordinary skill in the art using routine experimentation and/or as described herein.

The term "chromatography," as used herein, refers to a dynamic separation technique which separates the analyte of interest (e.g., an immunoglobulin) from other molecules in the mixture and allows it to be isolated. Typically, in a chromatography method, a mobile phase (liquid or gas) transports a sample containing the analyte of interest across or through a stationary phase (normally solid) medium. Differences in partition or affinity to the stationary phase separate different analytes while mobile phase carries the different analytes out at different time.

The term "affinity chromatography," as used herein, refers to a mode of chromatography where the analyte to be separated is isolated by its interaction with a molecule (e.g., an alkaline stable chromatography ligand) which specifically interacts with the analyte. In one embodiment, affinity chromatography involves the addition of a sample containing a target analyte (e.g., an immunoglobulin) to a solid support which carries on it an alkaline stable chromatography ligand, as described herein.

The term "protein A affinity chromatography," as used herein, refers to the separation or isolation of substances using protein A or SpA ligands, such as those described herein, where the SpA or protein A ligand is immobilized, e.g., on a solid support. Examples of protein A affinity chromatography media/resin known in the art include those having the protein A immobilized onto a controlled pore glass backbone, e.g., PROSEP A™ and PROSEP vA™ media/resin (Millipore); those having protein A immobilized onto a polystyrene solid phase, e.g., the POROS 50 A™ and Poros MabCapture A™ media/resin (Applied Biosystems, Inc.); and those having protein A immobilized on an agarose solid support, e.g., rPROTEIN A SEPHAROSE FAST FLOW™ or MABSELECT™ columns (Amersham Biosciences).

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by (β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The term "antigen-binding fragment" refers to a polypeptide portion of an immunoglobulin or antibody that binds an antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', F(ab')2, Fv, single chains, and single-chain antibodies.

Also encompassed are fusion proteins including an antibody or fragment thereof as a part of the fusion protein.

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding a variant of SpA.

The term "Fc-binding," "binds to an Fc portion" or "binding to an Fc portion" refers to the ability of an alkaline stable chromatography ligand described herein, to bind to the crystallizable part (Fc) of an antibody. In some embodiments, ligand according to the present invention binds an Fc portion of an antibody (e.g., human IgG1, IgG2 or IgG4) with an affinity of at least $10^{-7}$M, or at least $10^{-8}$ M, or at least $10^{-9}$M.

As used herein, the term "Fab binding" or "binding to a Fab portion" refers to the ability of an alkaline stable chromatography ligand described herein, to bind to a Fab region of an antibody or an immunoglobulin molecule. The term "reduced binding to a Fab portion" refers to any decrease in binding to a Fab (or $F(ab)_2$) portion of an immunoglobulin molecule by an SpA based ligand according to the present invention relative to the wt SpA, where the ligand further includes a mutation in one or more amino acids. In an exemplary embodiment, a ligand according to the present invention further includes the glycine residue at position 29 replaced with an alanine. In another embodiment, a ligand according to the present invention further includes the glycine at position 29 replaced with an amino acid other than alanine or tryptophan. In one embodiment, binding to a Fab portion of an immunoglobulin molecule is undetectable using conventional techniques in the art and those described herein. Binding to an immunoglobulin molecule can be detected using well known techniques including those described herein and including but not limited to, for example, affinity chromatography and Surface Plasmon Resonance Analysis. In some embodiments, an immunoglobulin binding protein encompassed by the present invention binds an immunoglobulin molecule with an affinity of at least $10^{-10}$ M.

II. Generation of SpA Based Molecules for Use as Chromatography Ligands

The SpA based chromatography ligands encompassed by the present invention can be made using any suitable methods known in the art.

For example, as an initial step, standard genetic engineering techniques, e.g., those described in the laboratory manual entitled Molecular Cloning by Sambrook, Fritsch and Maniatis, may be used for the generation of nucleic acids which express the SpA ligand molecules described herein.

In some embodiments, a nucleic acid molecule encoding one or more domains of SpA or portions thereof can be cloned into a suitable vector for expression in an appropriate host cell. Suitable expression vectors are well known in the art and typically include the necessary elements for the transcription and translation of the variant SpA coding sequence.

SpA molecules described herein may also be synthesized chemically from amino acid precursors for fragments using methods well known in the art, including solid phase peptide synthetic methods such as the Boc (tert-butyloxycarbonyl) or Fmoc (9-fluorenylmethyloxy carbonyl) approaches (see, e.g., U.S. Pat. Nos. 6,060,596; 4,879,378; 5,198,531; 5,240,680).

Expression of SpA molecules described herein can be accomplished in cells from eukaryotic hosts such as yeasts, insects or mammals, or in prokaryotic host cells, e.g., bacteria such as *E. coli*.

In some embodiments, SpA molecules or fragments and variants thereof may be expressed on the surface of a bacteriophage such that each phage contains a DNA sequence that codes for an individual SpA molecule displayed on the phage surface. The affinity of the SpA molecule for an immunoglobulin can be readily assayed for using standard techniques in the art and those described herein, e.g., ELISA and Biacore™ 2000 standard set-up (Biacore AB, Uppsala Sweden). It is desirable that the binding affinity of an SpA molecule of the present invention to an immunoglobulin is at least comparable with that of the parent molecule. Furthermore, it is desirable that the alkaline stability of the SpA molecule is generally improved over that of the parent molecule.

III. Assaying for Alkaline Stability of the SpA Molecules

Subsequent to the generation and purification of a suitable SpA ligand molecule, as described herein, the alkaline stability of the molecule can be assayed using standard techniques in the art and those described herein. For example, the alkaline stability of an SpA molecule according to the invention can assayed using routine treatment with NaOH at a concentration of about 0.5M, e.g., as described in the experimental part below.

In some embodiments, alkaline stable SpA molecules exhibit an "increased" or "improved" alkaline stability, meaning that the molecules are stable under alkaline conditions for an extended period of time relative to wild type SpA. Previously, it has been reported that SpA molecules based on the wild type C domain of SpA or having a mutation of one or more asparagine residues provides an improved chemical stability and hence a decreased degradation rate in environments wherein the pH is above about 10, such as up to about 13 or 14.

The present invention is based on the surprising and unexpected discovery of novel SpA molecules which exhibit increased alkaline stability even when they are based on domains other than the C domain or have mutations in amino acids other than asparagines. For example, the present invention provides B or Z domain based alkaline stable SpA molecules and SpA molecules which have a mutation in an amino acid at position n+1, where n represents an asparagine (e.g., asparagine at position 23).

In some embodiments, subsequent to the generation of the SpA ligands according to the present invention, alkaline stability of the ligands is evaluated using a novel high throughput immunological assay, described in more detail in the Examples infra. The assay is based on the assumption that degradation of SpA in response to extended caustic exposure is reflected as a loss or reduction in IgG binding. Briefly, soluble SpA based ligands are treated for about 6 hours with either water or 1.0M NaOH. Hydrophobic interactions are used to attach microgram quantities of neutralized candidate ligands to a solid support in the form of an ELISA plate, e.g., a 96 well plate. IgG binding is then assessed for each candidate ligand before and after exposure to 1.0M NaOH. Enhanced caustic stability is indicated when the amount of residual IgG binding to a ligand following caustic exposure exceeds that of wild type SpA or parental SpA from which it is derived.

IV. Supports Used for the Preparation of Chromatography Matrices

In some embodiments, alkaline stable SpA ligands encompassed by the present invention are attached to a support, e.g., a solid support or a soluble support, to generate a chromatography matrix suitable for the separation of biomolecules such as, e.g., immunoglobulins.

In some embodiments, a ligand according to the present invention is attached to a solid support. Without wishing to be bound by theory, it is contemplated that any suitable solid support may be used for the attachment of a ligand according to the invention. For example, solid support matrices include, but are not limited to, controlled pore glass, silica, zirconium oxide, agarose, polymethacrylate, polyacrylate, polyacrylamide, and polystyrene.

It is contemplated that any porous material that contributes to less than a 5% change in alkaline stability of the attached ligand after soaking for about 30 hours in 0.5 M NaOH may be used as a solid support.

A porous material used as a solid support may be comprised of a hydrophilic compound, a hydrophobic compound, an oleophobic compound, an oleophilic compound or any combination thereof. The porous material may be comprised of a polymer or a copolymer. Examples of suitable porous materials, include, but are not limited to polyether sulfone, polyamide, e.g., nylon, polysaccharides such as, for example, agarose and cellulose, polyacrylate, polymethacrylate, polyacrylamide, polymethacrylamide, polytetrafluoroethylene, polysulfone, polyester, polyvinylidene fluoride, polypropylene, polyethylene, polycarbonate, a fluorocarbon, e.g. poly (tetrafluoroethylene-co-perfluoro(alkyl vinyl ether)), glass, silica, zirconia, titania, ceramic, and metal.

The porous material may be comprised of an organic or inorganic molecules or a combination of organic and inorganic molecules and may be comprised of one or more functional groups, e.g., a hydroxyl group, a thiol group, an amino group, a carbonyl group, or a carboxylic acid group, suitable for reacting, e.g., forming covalent bonds for further chemical modification in order to covalently bond to a protein. In another embodiment, the porous material may not possess a functional group but can be coated with a layer of material that bears functional groups such as, an hydroxyl group, a thiol group, an amino acid group, a carbonyl group, or a carboxylic acid group.

In some embodiments, a conventional affinity separation matrix is used, e.g., of organic nature and based on polymers that expose a hydrophilic surface to the aqueous media used, i.e. expose hydroxy (—OH), carboxy (—COOH), carbonyl (—CHO, or RCO—R'), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agarose etc, which advantageously have been cross-linked, for instance with bisepoxides, epihalohydrins, 1,2,3-trihalo substituted lower hydrocarbons, to provide a suitable porosity and rigidity. In another embodiment, the solid support comprises porous agarose beads. The various supports used in the present invention can be readily prepared according to standard methods known in the art, such as, for example, inverse suspension gelation described, e.g., in Hjerten, *Biochim Biophys Acta* 79(2), 393-398 (1964). Alternatively, the base matrices can be commercially available products, such as Sepharose™ FastFlow (GE Healthcare, Uppsala, Sweden). In some embodiments, especially advantageous for large-scale separations, the support is adapted to increase its rigidity, and hence renders the matrix more suitable for high flow rates.

Alternatively, the solid support can be based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers can be easily produced according to standard methods, see e.g., Arshady, *Chimica e L'Industria* 70(9), 70-75 (1988). Alternatively, a commercially available product, such as Source™ (GE Healthcare, Uppsala, Sweden) and Poros (Applied BioSystems, Foster City, Calif.) may be used.

In yet other embodiments, the solid support comprises a support of inorganic nature, e.g. silica, zirconium oxide etc. The surface of inorganic matrices is often modified to include suitable reactive groups for further reaction to SpA and its variants. Examples include CM Zirconia (Ciphergen-BioSepra (CergyPontoise, France) and CPG® (Millipore).

In some embodiments, the polymers may, for instance, be based on zirconia or silica or controlled pore glass, which may be modified to either contain reactive groups and/or sustain caustic soaking, to be coupled to ligands.

Exemplary solid support formats include, but are not limited to, a bead, a gel, a membrane, a cassette, a column, a chip, a slide, a plate or a monolith.

With respect to the format of a matrix, in one embodiment, it is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used. Also, solid support in forms such as a surface, a chip, a capillary, or a filter may be used.

The matrix could also be in the form of membrane in a cartridge. The membrane could be in flat sheet, spiral, or hollow fiber format.

In another embodiment, a ligand according to the present invention is attached to a soluble support, e.g., a soluble polymer. Exemplary soluble supports include, but are not limited to, a bio-polymer such as, e.g., a protein or a nucleic acid. In some embodiments, biotin maybe used as a soluble polymer, e.g., as described in US Patent Publication No. 20080108053. For example, biotin may be bound to a ligand, e.g., an SpA based caustic stable ligand according to the present invention, which subsequent to being bound to the ligand can be used for isolating a protein of interest, e.g., an antibody or fragment thereof, e.g., present in a crude mixture and the protein of interest can be isolated or separated via precipitation of the biotin-ligand-protein polymer complex in either a reversible or irreversible fashion. The polymer may also be a synthetic soluble polymer, such as, for example, including but not limited to, a polymer containing negatively charged groups (carboxylic or sulfonic), positively charged groups (quarternary amine, tertiary amine, secondary or primary groups), hydrophobic groups (phenyl or butyl groups), hydrophilic groups (hydroxyl, or amino groups) or a combination of the above. Exemplary synthetic soluble polymers can be found in International PCT Publication No. WO2008091740 and U.S. Publication No. US20080255027, the entire teachings of each of which are incorporated by reference herein. These polymers, upon specific physical changes in one or more conditions such as pH, conductivity or temperature, can be used to purify the protein of interest via precipitation in either a reversible or an irreversible fashion. Synthetic soluble polymers may be used alone or may be coupled with a caustic stable ligand according to the present invention and used for capture/purification of a protein of interest such as, e.g., an antibody or a fragment thereof, via precipitation in either a reversible or an irreversible fashion.

V. Methods for Attaching a Ligand to a Support

Any suitable technique may be used for attaching a ligand to a support, e.g., a solid support including those well known in the art and described herein. For example, in some embodiments, the ligand may be attached to a support via conventional coupling techniques utilizing, e.g. amino and/or carboxy groups present in the ligand. For example, bisepoxides, epichlorohydrin, CNBr, N-hydroxysuccinimide (NHS) etc. are well-known coupling reagents. In some embodiments, a spacer is introduced between the support and the ligand, which improves the availability of the ligand and facilitates the chemical coupling of the ligand to the support. Alternatively, the ligand may be attached to the support by non-covalent bonding, such as physical adsorption or biospecific adsorption.

In various embodiments encompassed by the present invention, the ligand is attached to a solid support such as, for example, a chromatography resin at more than one site, thereby resulting in a chromatography matrix.

Attachment of an alkaline stable SpA based chromatography ligand to a solid support can be achieved via many different ways known, most of which are well known in the art, as well as those described herein. See, e.g., Hermanson et al., *Immobilized Affinity Ligand Techniques, Academic Press*, pp. 51-136 (1992).

For example, protein ligands can be coupled to a solid support via active groups on either the surface of the solid support or the protein ligand, such as, for example, hydrolxyl, thiol, epoxide, amino, carbonyl, epoxide, or carboxylic acid group. Attachment can be achieved using known chemistries including, but not limited to, use of cyanogen bromide (CNBr), N-hydroxyl succinimide ester, epoxy (bisoxirane) activation, and reductive amination.

For example, thiol directed protein coupling has been described in the literature. See, e.g., Ljungquist, et al. Eur. J. Biochem. Vol 186, pp. 558-561 (1989). This technique has been previously applied for coupling SpA to a solid support. Since wild type SpA does not contain thiol groups, the attachment is achieved by recombinantly inserting a thiol containing cysteine at the C-terminus of SpA. See, e.g., U.S. Pat. No. 6,399,750. Several commercial products such as MabSelect™, MabSelect™ Xtra and MabSelect™ SuRe are produced via this mechanism. It has been reported that this terminal cysteine only reacts with the epoxide group on the solid surface, thereby resulting in single point attachment of the SpA to the solid support. See, e.g., Process Scale Bioseparations for the Biopharmaceutical Industry, CRC Press, 2006, page 473.

In case of the present invention, in certain embodiments, SpA based chromatography ligands comprising two or more domains of SpA are attached to a solid support at more than one site via non-discriminate, multipoint attachment. In general, SpA contains abundant free amino groups from numerous lysines in each domain. The attachment of an SpA domain to more than one site on a solid support, e.g., a chromatography resin with epoxide or aldehyde group, can be achieved by reacting the amino group of lysine on SpA, via epoxide ring-opening or reductive amination, respectively. In certain embodiments, multipoint attachment can be achieved by the reaction of one or more naturally occurring amino acids on SpA having free hydroxyl groups, such as, for example, serine and tyrosine, with a support containing an epoxide group via a ring-opening reaction. Alternatively, multipoint attachment can be achieved, for example, by the reaction of naturally occurring amino acids on SpA having free carboxylic acid groups, such as, for example, aspartic acid and glutamic acid, with a support containing amino groups via, for example, N,N'-carbonyldiimidazole. Multipoint attachment of the ligand to support can also be achieved by a combination of all the above mechanisms.

To achieve caustic stability using the multimers of B and Z domains, this invention excludes the single cysteine mutation that leads to single point attachment.

SpA based chromatography ligands may also be attached to a solid support via an associative mechanism. For example, an associative group may interact with a ligand of interest non-covalently via ionic, hydrophobic or a combination of interactions, thereby to attach ligand of interest onto the solid surface. This facilitates the high efficiency coupling of ligand to the solid matrix, for example, as described in US Patent Publication No. 20070207500A1, thereby resulting in ligand density higher than that without the associative groups. Associative groups suitable for use in the invention include charged species such as ionic species, and uncharged species such as hydrophobic species. The associative group may modify the solid support, e.g. by covalently binding directly with the solid support. Suitable examples of ionic species may include quaternary amines, tertiary amines, secondary amines, primary amines, a sulfonic group, carboxylic acid, or any combination thereof. Suitable examples of hydrophobic species may include a phenyl group, a butyl group, a propyl group, or any combination thereof. It is also contemplated that mixed mode species may be used. The associative group may also interact with the protein ligand. Thus the interaction between the associative group and the protein ligand may be comprised of a mixture of interactions, e.g. ionic and hydrophobic species.

The associative group may be covalently coupled to the solid support by reacting a functional group on the solid support with a functional group on the associative group. Suitable functional groups include, but are not limited to amines, hydroxyl, sulfhydryl, carboxyl, imine, aldehyde, ketone, alkene, alkyne, azo, nitrile, epoxide, cyanogens and activated carboxylic acid groups. As an example, agarose beads contain hydroxyl groups which may be reacted with the epoxide functionality of a positively charged associative group, such as glycidyl trimethylammonium chloride. A skilled artisan will appreciate that a plurality of associative groups may be coupled to the solid support provided that at least one bifunctional associative group is used. Thus associative groups may be coupled in tandem to the solid support or they may be individually coupled directly to the solid support.

In some embodiments, the present invention provides associative groups and/or protein ligands which may be coupled to a solid support via an intervening linker. The linker may comprise at least one functional group coupled to a linking moiety. The linking moiety may comprise any molecule capable of being coupled to a functional group. For example, the linking moiety may include any of an alkyl, an alkenyl, or an alkynyl group. The linking moiety may comprise a carbon chain ranging from 1 to 30 carbon atoms. In some embodiments the linker may be comprised of more than 30 carbon atoms. The linking moiety may comprise at least one hetero-atom such as nitrogen, oxygen and sulfur. The linking moiety may be comprised of a branched chain, an unbranched chain or a cyclic chain. The linking moiety may be substituted with two or more functional groups.

Choosing the appropriate buffer conditions for coupling a protein ligand to a solid support is well within the capability of the skilled artisan. Suitable buffers include any non-amine containing buffer such as carbonate, bicarbonate, phosphate and acetate buffers. When associative chemistry is used, salt concentration of the buffer will depend on the associative group used. For example, the salt concentration may be in the range of 5 nM-100 mM. Where a charged species is used, the salt concentration may be at least 5 nM but less than 0.1M, at least 5 nM but less than 0.01M, at least 5 nM but less than 0.001M. In certain embodiments, the salt concentration may be 0.01M. Where a hydrophobic species is used a high salt concentration is usually desirable. Thus the salt concentration may be greater than 0.001 M, greater than 0.01 M, or greater than 0.1 M.

In some embodiments, when associative chemistry is used, the reaction is performed at a temperature ranging from 0° C. to 99° C. In certain embodiments the reaction method is practiced at a temperature less than 60° C., less than 40° C., less than 20° C., or less than 10° C. In some embodiments the method of the invention is practiced at a temperature of about 4° C. In other embodiments the method of the invention is practiced at a temperature of 20° C.

VI. Methods for Assaying for Alkaline Stability of the Attached Ligands

The increased alkaline stability of the ligands subsequent to their attachment to a support can be assayed by using well known techniques in the art and those described herein. For example, in some embodiments, alkaline stability of multimers of SpA domains attached to a resin, e.g., B and Z domains of SpA attached to a chromatography resin, as described herein, can be confirmed by treatment of the resin with 0.5 M NaOH. It is to be understood that an increased stability means that the initial IgG binding capacity is retained during a longer period of time than what can be achieved by the wild type SpA molecule. For example, in case of the present invention, after 100 cycles, each including a 15 min treatment with 0.5 N NaOH, the percentage of retained capacity of the SpA ligands, e.g., those comprising multiple B or Z domains, is at least 1.5 times more, 2.0 times more, 2.5 times more, or 3 times more than that of wild type SpA. In one embodiments, the alkaline stability of the bound ligand, as assayed by the retention of IgG binding capacity over time, is measured as follows. The binding capacity, referred to as Qd 50%, is measured by obtaining the volume of IgG loaded to a $UV_{280nm}$ of 50% of the initial IgG concentration. Qd 50% of the initial virgin resin packed in a column is measured first. The resin is then exposed to about 10 cycles of 15 min exposure of 0.5 N NaOH at 0.8 ml/min. Qd 50% is measured again. This process is repeated until the resin is exposed to a total of about 100 cycles of 0.5 N NaOH. Qd 50% is measured one last time and the results from resins made from different ligands are compared with the wildtype SpA.

In another assay, caustic or alkaline stability of the resins is measured by static soaking of resins of interest. By soaking a measured amount of resin in 0.5N NaOH for 25 hrs with gentle rotation and measuring IgG binding capacity before and after the NaOH soaking, the alkaline stability by way of retention of binding capacity of the resin can be determined.

VII. Methods of Purifying a Target Molecule Using a Chromatography Ligand of the Invention In some embodiments, the present invention provides a method of purifying a target molecule from a mixture using the alkaline stable chromatography ligands described herein. The target molecule may be any molecule which is recognized by an alkaline stable chromatography ligand provided herein, where the ligand is coupled to a solid support. Examples of target molecules include immunoglobulins. The immunoglobulins may be polyclonal antibodies or a monoclonal antibody or a functional fragment thereof. Functional fragments include any fragment of an immunoglobulin comprising a variable region that still binds specifically to its antigen while at the same time retaining its ability to specifically bind to a protein ligand coupled to a solid support.

In some embodiments, a method of isolating a target molecule of interest using an alkaline stable chromatography ligand described herein includes the steps of: (a) contacting a solid support including an attached SpA based alkaline stable chromatography ligand with a mixture comprising a molecule of interest under conditions such that the target molecule specifically binds to the ligand; and (b) altering the conditions such that the target molecule is no longer bound to the ligand, thereby isolating the target molecule.

In some embodiments, the altering step includes altering the pH, such the target molecule is no longer bound to the ligand. In a particular embodiment, the pH is altered in a manner such that it is more acidic than the pH conditions in step (a). For example, in one embodiment, step (a) may be performed at a neutral pH, or a pH ranging from about 6 to about 8 and step (b) may be performed at an acidic pH, e.g., a pH ranging from about 1 to about 5.

In another embodiment, step (b) comprises altering the salt concentration of the buffer in use, such that the target molecule is no longer bound to the ligand. For example, in one embodiment, a high salt concentration, e.g., >0.1 M, may be used in step (a) and a lower salt concentration, e.g., <0.1M may be used in step (b). Conversely, in some embodiments, a low salt concentration, e.g., <0.1M may be used in step (a) and a high salt concentration may be used in step (b). In still other embodiments both the pH and the salt concentration of the buffer may be altered between step (a) and step (b).

One skilled in the art can readily determine the conditions suitable for binding a target molecule to a ligand, and thereby alter the conditions to disrupt the binding of the molecule to the ligand.

This invention is further illustrated by the following examples which should not be construed as limiting. The contents of all references, patents and published patent applications cited throughout this application, as well as the Figures, are incorporated herein by reference.

EXAMPLES

Example 1: Generation of an SpA B Domain Variant Having an n+1 Mutation, where n Represents an Asparagine In an exemplary experiment, a synthetic gene encoding the "B domain" of protein A is obtained from DNA 2.0 (Menlo Park, Calif.). The 5' end of the gene includes a codon for an initiating methionine as well as six histidine codons at the 3' end of the gene. The gene is provided in vector pJ56:8620 from DNA 2.0. The parent vector pJ56 confers resistance to ampicillin, kanamycin, chloramphenicol and gentamicin. Appropriate restriction enzyme sites for the subsequent cloning of the gene into expression vectors are introduced into the gene at both 5' and 3' ends. A plasmid map of the vector is shown in FIG. 5.

Saturation mutagenesis is subsequently used to mutate glutamic acid at position 24 to all other naturally occurring amino acids except cysteine (C), serine (S), alanine (A), glycine (g), asparagine (N), and glutamine (Q) by PCR-based methods using the Phusion High-Fidelity DNA polymerase (New England Biolabs, Ipswich, Mass.). Primers are purchased from IDT DNA (Coralville, Iowa), as 100 µM solution in Tris EDTA buffer. The mutagenic primers have the sequence CTGCCGAACCTGAACNN SGAACAAC-GCAACGG (SEQ ID NO: 41) where NNS represents the three bases encoding the amino acid at position 24. PCR is performed in 50 µL reactions containing dNTPs (0.2 mM each), 125 ng of each primer, 50 ng of template plasmid, and 1 U of Phusion enzyme. PCR is carried out according to the scheme outlined in Table III.

TABLE III

| Cycle description | Temperature | Time | # of cycles |
| --- | --- | --- | --- |
| Initial denaturation | 95° C. | 30 seconds | 1 cycle |
| Denaturation | 95° C. | 30 seconds | 18 cycles |
| Annealing | 55° C. | 60 seconds | |
| Extension | 68° C. | 6 minutes | |

PCR reactions are treated with the restriction enzyme DpnI (New England Biolabs, Ipswich, Mass.) to reduce wild type background. To each 50 µL PCR reaction, about 1 µL of DpnI enzyme is added and the samples are incubated for about one hour at 37° C.

E. coli NEB5α competent cells (New England Biolabs, Ipswich, Mass.) are transformed with 2 µL of the DpnI-treated PCR reaction. Cells are thawed on ice, and 2 µL of the PCR reaction is added to 25 µL of cells. Following about a 30 minute incubation on ice, cells are heat shocked for 30 seconds at about 42° C. Cells are allowed to recover for about 5 minutes on ice, and then 125 µL of SOC media (New England BioLabs) is added. Cells are incubated for about one hour at 37° C., and then 100 µL are plated on LB plates (Northeast Laboratory Services, Winslow, Me.) containing 100 µg/mL ampicillin and grown overnight at about 37° C. Positive clones are identified by testing for the expression of the proteins in total cell lysates using SDS PAGE.

In order to obtain purified DNA, individual colonies are picked for overnight culture in LB containing 100 µg/mL ampicillin. DNA is purified using spin mini-prep kits from Qiagen (Valencia, Calif.).

Mini-prepped DNA is sequenced to confirm the identity of each clone (MWG Biotech, Huntsville Ala.). The resulting plasmid is used to transform E. coli NEB5a competent cells as described above.

Following the identification of positive clones, 35 mls overnight cultures are grown in Terrific Broth with 100 µg/ml ampicillin and cells are pelleted by centrifugation at 13,500 g for 10 minutes. Pellets are resuspended in 10 mls of 20 mM imidazole in PBS (phosphate buffered saline), lysed by sonication and centrifuged at 13,500 g for 30 minutes to pellet insoluble debris. Lysates are subsequently applied to 750 µl of Ni-NTA resin that is pre-equilibrated with 10 column volumes of 20 mM imidazole in PBS. After washing with 20 column volumes of 20 mM imidazole in PBS, samples are eluted from the resin with 200 mM imidazole in PBS. Purified protein is dialyzed overnight against PBS using Pierce Slide-A-Lyzer 3.5 MWCO dialysis cassettes. Following dialysis, total protein quantitation is accomplished using the Pierce MicroBCA assay, and samples are stored at −30° C.

The amino acid and nucleic acid sequences for the wt his-tagged B domain and the various n+1 mutants are depicted in FIGS. 6 and 7.

Example 2: Assaying the Expressed Proteins for Alkaline Stability

Affinity purified wildtype and mutant SpA his-tagged constructs described in Example 1 are diluted with MilliQ water or with NaOH to a final concentration of 1N and incubated for six hours at room temperature. Biorad Micro Biospin 6 gel filtration columns are used to neutralize and buffer exchange 50 µl of each sample into PBS. Total protein quantitation is accomplished using the Pierce MicroBCA assay and samples are diluted to 10 µg/ml in PBS for loading onto the ELISA plate. Approximately 200 µl (2 µg) of treated PrA is adsorbed to the wells of an ELISA plate for 2-24 hours at 37° C. Plates are blocked in Pierce Superblock Blocking Buffer in PBS (Superblock-PBS) for about 2 hours at room temperature. Approximately 200 µl of Sigma human gamma globulin diluted to 0.05 mg/ml in Superblock-PBS (10 µg) is added to each well of the plate and binding is allowed to proceed for about 1 hour at room temperature. Following three washes with PBS containing about 0.05% Tween20 (PBS-T), plates are incubated with 200 µl of a 1:10,000 dilution of a chicken IgY-HRP conjugate raised against human IgG for about 1 hour at room temperature. After the final three washes with PBS-T, plates are developed with 100 µl of Pierce 1-Step Slow TMB ELISA for 30 minutes at room temperature. The reaction is stopped by the addition of 100 µl of 1N HCL and primary IgG binding is quantitated as absorbance read at 450 nm. All samples are assayed in triplicate and data is analyzed as the change in primary IgG binding before and after caustic treatment.

Figure 8:
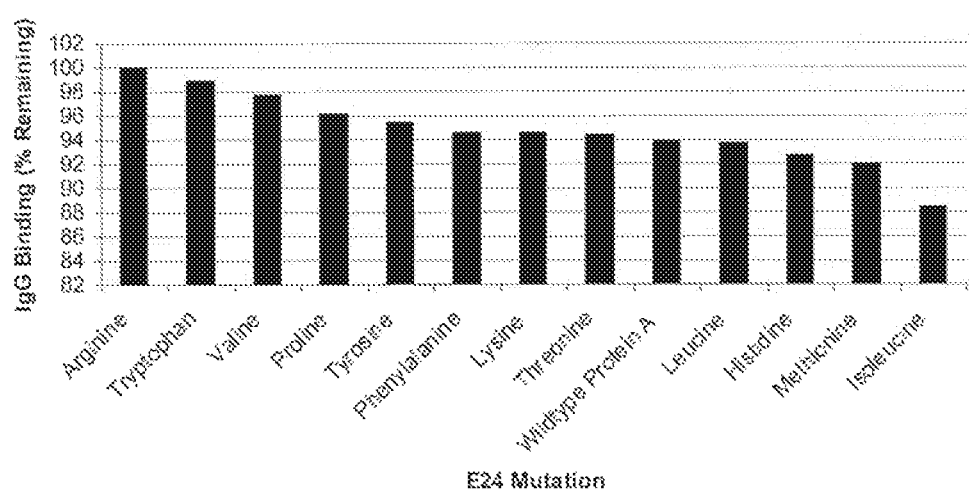
FIG. 8 depicts a bar graph summarizing the results of an exemplary experiment to assay for residual IgG binding in the various his-tagged n+1 B domain mutants, where n represents the asparagine at position 23, using the high-throughput ELISA based assay described herein. The X-axis represents various n+1 B domain mutants having a mutation at position 24 and the Y-axis represents the percent IgG binding remaining after a six hour exposure to 1N NaOH. As shown in the graph, n+1 B domain mutants having amino acids which contain bulky side chains at position 24 exhibit increased caustic stability relative to the wt B domain.

The result of an exemplary experiment assaying for the alkaline stability of the various n+1 B domain mutants is summarized in the bar graph in FIG. 8. The various constructs are depicted on the X-axis and the corresponding percent of IgG binding remaining after six hours of exposure to 1M NaOH is plotted on the Y-axis As depicted in the bar graph in FIG. 8, several of the n+1 mutants having a bulky amino acid at position 24 of the B domain exhibit enhanced caustic stability.

In another experiment, SpA ligands having two or more B domains or two or more Z domains of SpA are assayed for alkaline stability using the assay described above. In yet another experiment, SpA ligands having three B domains (B3), four B domains (B4), five B domains (B5), six B domains (B6) or seven B domains (B7) are assayed for alkaline stability using the assay described above.

In an exemplary experiment, the percent of residual IgG binding capacity of the ligands B3, B4 and B5, as assayed using the ELISA based method described herein is as follows. The B3 ligand retains about 79% of its residual IgG binding capacity following a six hour exposure to 1M NaOH; the B4 ligand retains about 86% of its residual IgG binding capacity following a six hour exposure to 1M NaOH; and the B5 ligand retains about 83% of its residual IgG binding capacity following a six hour exposure to 1M NaOH. The wt SpA ligand (nPrA) only retains about 49% of its residual IgG binding capacity following a six hour exposure to 1M NaOH.

Example 3: Attachment of Wildtype SpA and SpA Variants to a Solid Support

Subsequent to the generation of the various SpA variants and identification of those which are caustic stable using one or more assays known in the art and those described in Example 2, the SpA variants are attached to a support, e.g., a solid support. In an exemplary experiment, agarose beads (Sepharose 4B) (GE Healthcare, Piscataway N.J.) are crosslinked using epichlorohydrin according to a previously described method (Porath and Fornstedt, *J. Chromatography*, 51:479 (1979)). The agarose beads are reacted with positively charged associative groups, e.g., cations, according to the following method: 50 mL of beads are added to 40 g of 75% wt glycidyl trimethylammonium chloride (GT-MAC), 10 mL water (Millipore Corp., Billerica, Mass.) and 1.67 g 50 wt sodium hydroxide. The reaction is shaken vigorously (>100 rpm) on a rotary shaker overnight at room temperature. The beads are then filtered and washed with three 100 mL volumes of water (Millipore Corp, Billerica, Mass.).

The beads (50 mL, filtered cake) are added to ajar containing 15 mLs of 4.6M NaOH. The mixture is slurried and then 19.5 mL of butanediol diglycidylether (BUDGE) is added. This mixture is shaken at 35° C. for about 2 hours. The beads are then washed with 750 mL of water (Millipore Corp, Billerica, Mass.) and equilibrated with 250 mL of 10 mM NaHCO$_3$.

Immediately following the BUDGE activation step, 10 mL of the filtered bead cake is added to 10 mL solution of 10 mM NaHCO$_3$ containing a 15 g/L concentration of wild type SpA or an SpA ligand according to the present invention. The mixture is capped in a glass vial and the vial is rotated in a hybridizer at 37° C. for about 2 hours. After two hours, the beads are washed with 30 mLs of water (Millipore Corp, Billerica, Mass.). The filtered bead cake (10 mL) is added to a jar containing a 10 mL solution comprised of 1 mL of thioglycerol and 9 mL of a buffer solution with 0.2 M NaHCO$_3$ and 0.5 M NaCl. The mixture is slurried and rotated overnight at room temperature. The beads are then washed with 30 mL of the following buffers: 0.1 M Tris Buffer (pH 8), 0.1 M Tris Buffer with 0.15 M NaCl (pH 8), 50 mM Acetic Acid (pH 4.5), PBS (pH 7.4) with 0.002% sodium azide.

Resin samples coupled with different SpA variants are labeled as follows: nPrA for wild type SpA; Z3 for SpA ligand containing three Z domains; E3 for SpA ligand containing three E domains; D3 for SpA ligand containing three D domains; A3 for SpA ligand containing three A domains, C3 for SpA ligand containing three C domains; B3 for SpA ligand containing three B domains; B4 for SpA ligand containing four B domains; B5 for SpA ligand containing 5 B domains; B5NF and B7NF containing 5 and 7 B domains, respectively, and additionally containing a G29A mutation at position 29. Following attachment to a resin, the various SpA variants are assayed for alkaline stability.

Example 4: Resin IgG Binding Capacity (Qd 50%) Tests Before and after Caustic Cycling In an exemplary experiment, the various SpA constructs according to the invention are assayed for the IgG binding capacity following attachment to a support. In one exemplary experiment, a standard method for testing resin/media dynamic capacity using commercial polyclonal IgG is used. Briefly, resin coupled with an SpA ligand according to the present invention is packed into an Omnifit column (6.6 mm×70 mm) in PBS, pH 7.4 and the flow rate is set at 300 cm/hr. The packed column is equilibrated with PBS for 10 column volumes (CVs). Polyclonal IgG (Sigma-Aldrich, 2 mg/mL in PBS, pH 7.4) is loaded onto the column until UV$_{280nm}$ reaches more than 50% of the initial IgG concentration. After washing with equilibration buffer, IgG is eluted with 0.1 M citric acid, pH 3.0. After each run, the media is sanitized using 6M Guanidinine hydrochloride. Qd 50% is calculated based on the amount of IgG loaded when UV$_{280nm}$ reaches 50% of the initial IgG concentration.

After the initial dynamic capacity measurement, the media is exposed to 10 cycles of 15 min, 0.5 N NaOH (flow rate 100 cm/hr) followed by another IgG dynamic capacity measurement. The media is subsequently contacted with another 10 cycles of 15 min, 0.5N NaOH exposure, followed by another dynamic binding capacity measurement. Dynamic capacity measurement is carried out after each sample is exposed to 100 cycles of 15 min 0.5 N NaOH.

In an exemplary experiment, the results of which are depicted in FIG. 9, trimers of E, D, A, B, C, and Z domains containing natural B domain linkers are attached to an agarose resin and their caustic stability is measured by dynamic binding capacity over 100 cycles of caustic exposure, each cycle including a 15 minute exposure to 0.5 N NaOH. As summarized in the graph in FIG. 9, the number of cycles are plotted on the X-axis and the IgG binding capacity is plotted on the Y-axis. The C and the Z domain trimers exhibit approximately the same level of caustic stability. The B domain trimers are more caustic stable than the A domain trimers, which are more caustic stable than the E and the D domain trimers. Therefore, the order of caustic stability can be summarized as follows C and Z>B>A>E and D.

In another exemplary experiment, agarose resins coupled with B domain variants: BBB (B3), BBBB (B4), BBBBB (B5), BBBBB-NF (B5-NF), and BBBBBBB-NF (B7-NF), are compared with wt SpA (nPrA) using the assay described above to assay for IgG dynamic binding capacity over 100 cycles of caustic exposure, each cycle including a 15 minute exposure to 0.5 N NaOH. As summarized in the graph in FIG. 10, the extent of caustic stability is directly proportional to the number of domains and further that, the G29A mutation to reduce Fab binding does not affect the caustic stability.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. An alkaline-stable chromatography ligand comprising two or more C domains of *Staphylococcus* protein A (SpA) attached to a chromatography resin at more than one site on the resin, wherein each C domain comprises the amino acid sequence set forth in SEQ ID NO:11 having a mutation to replace the glycine at position 29 with an amino acid other than alanine or tryptophan to reduce Fab binding, as shown in SEQ ID NO: 44, wherein the ligand retains at least 95% of its binding capacity after 5 hours incubation in 0.5 M NaOH.

2. The alkaline-stable chromatography ligand of claim 1, wherein the ligand comprises three or more C domains.

3. The alkaline-stable chromatography ligand of claim 1, wherein the ligand comprises four or more C domains.

4. The alkaline-stable chromatography ligand of claim 1, wherein the ligand comprises five or more C domains.

5. The alkaline-stable chromatography ligand of claim 1, wherein the ligand comprises six or more C domains.

6. The alkaline-stable chromatography ligand of claim 1, wherein the ligand comprises seven or more C domains.

7. A chromatography matrix comprising a ligand according to claim 1.

8. The ligand according to claim 1, wherein the ligand is capable of binding at least 1.5 times, or 2 times, or 3 times, or more of IgG as compared to wt SpA, following exposure to 0.5M NaOH for at least 5 hours.

9. A caustic stable affinity chromatography matrix comprising a ligand comprising three or more, or four or more, or five or more, or six or more, or seven or more C domains of *Staphylococcus* protein A (SpA) attached to a solid support via multipoint attachment, wherein each C domain comprises the amino acid sequence set forth in SEQ ID NO:11 having a mutation to replace the glycine at position 29 with an amino acid other than alanine or tryptophan to reduce Fab binding, as shown in SEQ ID NO: 44, wherein the ligand retains at least 95% of its binding capacity after 5 hours incubation in 0.5 M NaOH.

10. The caustic stable chromatography matrix of claim 9, wherein the solid support is selected from the group consisting of controlled pore glass, polyvinyl alcohol, zirconium oxide, agarose, polymethacrylate, polyacrylate, polyacrylamide and polystyrene.

11. A caustic stable affinity chromatography ligand comprising three C domains (C3) or four C domains (C4), or five C domains (C5), or six C domains (C6), or seven C domains (C7) of *Staphylococcus* protein A (SpA) attached to a solid support via multipoint attachment, wherein each C domain comprises the amino acid sequence set forth in SEQ ID NO:11 having a mutation to replace the glycine at position 29 with an amino acid other than alanine or tryptophan to reduce Fab binding, as shown in SEQ ID NO: 44, and wherein the extent of caustic stability of ligand is in the order of C3<C4<C5<C6<C7, following exposure of ligand to 0.5M NaOH for at least 5 hours.

* * * * *

SEQUENCE LISTING

```
<160> NUMBER OF SEQ ID NOS: 44

<210> SEQ ID NO 1
<211> LENGTH: 159
<212> TYPE: DNA
<213> ORGANISM: Staphylococcus aureus

<400> SEQUENCE: 1
gcgcaacaaa acgctttcta tcaggtactg aacatgccta acctgaacgc cgatcagcgt      60
aacggcttca tccaaagcct gaaggacgac ccgagccagt ccgcaaacgt tctgggtgaa     120
gctcaaaaac tgaacgacag ccaggcaccg aaagctgac                           159

<210> SEQ ID NO 2
<211> LENGTH: 177
<212> TYPE: DNA
<213> ORGANISM: Staphylococcus aureus

<400> SEQUENCE: 2
gcccaacaga acaaatttaa caaagaccag cagtccgcgt tctacgagat tctgaacatg      60
cctaacctga atgaagaaca gcgcaacggt tttattcagt ctctgaagga cgatccttct    120
caatccacca acgtactggg cgaagcgaag aaactgaacg aatctcaggc tccgaag       177

<210> SEQ ID NO 3
<211> LENGTH: 174
<212> TYPE: DNA
<213> ORGANISM: Staphylococcus aureus
```

<400> SEQUENCE: 3

```
gccgacaaca acttcaacaa agagcagcaa aacgctttct acgaaatcct gaatatgcca      60
aatctgaacg aagagcagcg taacggtttc atccaatctc tgaaagacga tccgtcccag    120
tccgcgaatc tgctggcgga ggctaaaaag ctgaacgaat cccaggctcc gaaa           174
```

<210> SEQ ID NO 4
<211> LENGTH: 174
<212> TYPE: DNA
<213> ORGANISM: Staphylococcus aureus

<400> SEQUENCE: 4

```
gcagacaata agttcaataa agagcagcag aacgcatttt acgagatcct gcatctgccg      60
aacctgaacg aagaacaacg caacggtttc attcagagcc tgaaagacga cccatctcag    120
tccgctaacc tgctggcgga agcaaagaag ctgaacgatg cacaggcgcc gaaa           174
```

<210> SEQ ID NO 5
<211> LENGTH: 174
<212> TYPE: DNA
<213> ORGANISM: Staphylococcus aureus

<400> SEQUENCE: 5

```
gcggataaca aattcaacaa ggagcaacag aacgcattct atgaaattct gcacctgccg      60
aatctgacgg aggagcaacg taacggctttt atccagtccc tgaaggatga tccgtctgtg    120
tctaaagaga tcctggcgga ggcaaaaaaa ctgaatgatg cacaagctcc gaaa           174
```

<210> SEQ ID NO 6
<211> LENGTH: 174
<212> TYPE: DNA
<213> ORGANISM: Staphylococcus aureus

<400> SEQUENCE: 6

```
gtagacaaca aattcaataa agaacagcag aacgctttct atgaaatcct gcacctgccg      60
aacctgaacg aagaacagcg taacgcgttt atccagtccc tgaaagacga cccgagccag    120
agcgcaaatc tgctggcgga agcgaaaaag ctgaacgatg cccaggcgcc gaaa           174
```

<210> SEQ ID NO 7
<211> LENGTH: 51
<212> TYPE: PRT
<213> ORGANISM: Staphylococcus aureus

<400> SEQUENCE: 7

```
Ala Gln Gln Asn Ala Phe Tyr Gln Val Leu Asn Met Pro Asn Leu Asn
 1               5                  10                  15
Ala Asp Gln Arg Asn Gly Phe Ile Gln Ser Leu Lys Asp Asp Pro Ser
            20                  25                  30
Gln Ser Ala Asn Val Leu Gly Glu Ala Gln Lys Leu Asn Asp Ser Gln
        35                  40                  45
Ala Pro Lys
    50
```

<210> SEQ ID NO 8
<211> LENGTH: 61
<212> TYPE: PRT
<213> ORGANISM: Staphylococcus aureus

<400> SEQUENCE: 8

```
Ala Asp Ala Gln Gln Asn Lys Phe Asn Lys Asp Gln Gln Ser Ala Phe
```

```
                1               5                       10                      15
              Tyr Glu Ile Leu Asn Met Pro Asn Leu Asn Glu Glu Gln Arg Asn Gly
                                    20                      25                      30
              Phe Ile Gln Ser Leu Lys Asp Asp Pro Ser Gln Ser Thr Asn Val Leu
                              35                      40                      45
              Gly Glu Ala Lys Lys Leu Asn Glu Ser Gln Ala Pro Lys
                      50                      55                      60
```

<210> SEQ ID NO 9
<211> LENGTH: 58
<212> TYPE: PRT
<213> ORGANISM: Staphylococcus aureus

<400> SEQUENCE: 9

```
              Ala Asp Asn Asn Phe Asn Lys Glu Gln Gln Asn Ala Phe Tyr Glu Ile
                1               5                       10                      15
              Leu Asn Met Pro Asn Leu Asn Glu Glu Gln Arg Asn Gly Phe Ile Gln
                                    20                      25                      30
              Ser Leu Lys Asp Asp Pro Ser Gln Ser Ala Asn Leu Leu Ala Glu Ala
                              35                      40                      45
              Lys Lys Leu Asn Glu Ser Gln Ala Pro Lys
                      50                      55
```

<210> SEQ ID NO 10
<211> LENGTH: 58
<212> TYPE: PRT
<213> ORGANISM: Staphylococcus aureus

<400> SEQUENCE: 10

```
              Ala Asp Asn Lys Phe Asn Lys Glu Gln Gln Asn Ala Phe Tyr Glu Ile
                1               5                       10                      15
              Leu His Leu Pro Asn Leu Asn Glu Glu Gln Arg Asn Gly Phe Ile Gln
                                    20                      25                      30
              Ser Leu Lys Asp Asp Pro Ser Gln Ser Ala Asn Leu Leu Ala Glu Ala
                              35                      40                      45
              Lys Lys Leu Asn Asp Ala Gln Ala Pro Lys
                      50                      55
```

<210> SEQ ID NO 11
<211> LENGTH: 58
<212> TYPE: PRT
<213> ORGANISM: Staphylococcus aureus

<400> SEQUENCE: 11

```
              Ala Asp Asn Lys Phe Asn Lys Glu Gln Gln Asn Ala Phe Tyr Glu Ile
                1               5                       10                      15
              Leu His Leu Pro Asn Leu Thr Glu Glu Gln Arg Asn Gly Phe Ile Gln
                                    20                      25                      30
              Ser Leu Lys Asp Asp Pro Ser Val Ser Lys Glu Ile Leu Ala Glu Ala
                              35                      40                      45
              Lys Lys Leu Asn Asp Ala Gln Ala Pro Lys
                      50                      55
```

<210> SEQ ID NO 12
<211> LENGTH: 58
<212> TYPE: PRT
<213> ORGANISM: Staphylococcus aureus

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
65

<210> SEQ ID NO 14
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Asp Asn Lys Phe Asn Lys Glu Gln Gln Asn Ala Phe Tyr Glu
1               5                   10                  15

Ile Leu His Leu Pro Asn Leu Asn Met Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
65

<210> SEQ ID NO 15
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Asp Asn Lys Phe Asn Lys Glu Gln Gln Asn Ala Phe Tyr Glu
1               5                   10                  15

Ile Leu His Leu Pro Asn Leu Asn Ile Glu Gln Arg Asn Gly Phe Ile

-continued

```
                20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 16
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Asp Asn Lys Phe Asn Lys Glu Gln Gln Asn Ala Phe Tyr Glu
 1               5                  10                  15

Ile Leu His Leu Pro Asn Leu Asn Phe Glu Gln Arg Asn Gly Phe Ile
                20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 17
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Asp Asn Lys Phe Asn Lys Glu Gln Gln Asn Ala Phe Tyr Glu
 1               5                  10                  15

Ile Leu His Leu Pro Asn Leu Asn Thr Glu Gln Arg Asn Gly Phe Ile
                20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 18
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Asp Asn Lys Phe Asn Lys Glu Gln Gln Asn Ala Phe Tyr Glu
 1               5                  10                  15

Ile Leu His Leu Pro Asn Leu Asn Pro Glu Gln Arg Asn Gly Phe Ile
                20                  25                  30
```

```
Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 19
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Asp Asn Lys Phe Asn Lys Glu Gln Gln Asn Ala Phe Tyr Glu
 1               5                  10                  15

Ile Leu His Leu Pro Asn Leu Asn Trp Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 20
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Asp Asn Lys Phe Asn Lys Glu Gln Gln Asn Ala Phe Tyr Glu
 1               5                  10                  15

Ile Leu His Leu Pro Asn Leu Asn Arg Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
 65

<210> SEQ ID NO 21
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Asp Asn Lys Phe Asn Lys Glu Gln Gln Asn Ala Phe Tyr Glu
 1               5                  10                  15

Ile Leu His Leu Pro Asn Leu Asn Val Glu Gln Arg Asn Gly Phe Ile
            20                  25                  30
```

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
65

<210> SEQ ID NO 22
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Asp Asn Lys Phe Asn Lys Glu Gln Gln Asn Ala Phe Tyr Glu
1               5                   10                  15

Ile Leu His Leu Pro Asn Leu Asn Leu Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
65

<210> SEQ ID NO 23
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Asp Asn Lys Phe Asn Lys Glu Gln Gln Asn Ala Phe Tyr Glu
1               5                   10                  15

Ile Leu His Leu Pro Asn Leu Asn Tyr Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
    50                  55                  60

His
65

<210> SEQ ID NO 24
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Asp Asn Lys Phe Asn Lys Glu Gln Gln Asn Ala Phe Tyr Glu
1               5                   10                  15

Ile Leu His Leu Pro Asn Leu Asn His Glu Gln Arg Asn Gly Phe Ile
            20                  25                  30

Gln Ser Leu Lys Asp Asp Pro Ser Gln Ser Ala Asn Leu Leu Ala Glu

```
                    35                  40                  45

Ala Lys Lys Leu Asn Asp Ala Gln Ala Pro Lys His His His His His
        50                  55                  60

His
 65

<210> SEQ ID NO 25
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Asp Asn Lys Phe Asn Lys Glu Gln Gln Asn Ala Phe Tyr Glu
 1               5                  10                  15

Ile Leu His Leu Pro Asn Leu Asn Lys Glu Gln Arg Asn Gly Phe Ile
                20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
        50                  55                  60

His
 65

<210> SEQ ID NO 26
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Asp Asn Lys Phe Asn Lys Glu Gln Gln Asn Ala Phe Tyr Glu
 1               5                  10                  15

Ile Leu His Leu Pro Asn Leu Asn Asp Glu Gln Arg Asn Gly Phe Ile
                20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys His His His His His
        50                  55                  60

His
 65

<210> SEQ ID NO 27
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gaattctaat acgactcact ataacgcgtc cacaacggtt ccctctaga aataatttg      60 tttaactttaa agaaggagat atacatatgg cagacaataa gttcaataaa gagcagcaga     120
acgcatttta cgagatcctg ctctgccgaa cctgaacgaa gaacaacgca acggtttcat     180
tcagagcctg aaagacgacc catctcagtc cgctaacctg ctggcggaag caaagaagct     240
```
gaacgatgca caggcgccga acatcatca ccatcaccac taataaggat cc     292

<210> SEQ ID NO 28
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgatggaa gaacaacgca acggtttcat    180
tcagagcctg aaagacgacc catctcagtc cgctaacctg ctggcggaag caaagaagct    240
gaacgatgca caggcgccga acatcatca ccatcaccac taataaggat cc            292

<210> SEQ ID NO 29
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgatagaa gaacaacgca acggtttcat    180
tcagagcctg aaagacgacc catctcagtc cgctaacctg ctggcggaag caaagaagct    240
gaacgatgca caggcgccga acatcatca ccatcaccac taataaggat cc            292

<210> SEQ ID NO 30
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgttcgaa gaacaacgca acggtttcat    180
tcagagcctg aaagacgacc catctcagtc cgctaacctg ctggcggaag caaagaagct    240
gaacgatgca caggcgccga acatcatca ccatcaccac taataaggat cc            292

<210> SEQ ID NO 31
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaattctaat acgactcact ataacgcgtc cacaacggtt ccctctaga aataattttg     60 tttaacttta agaaggagat atacatatgg cagacaataa gttcaataaa gagcagcaga    120

```
acgcatttta cgagatcctg ctctgccgaa cctgacagaa gaacaacgca acggtttcat    180
tcagagcctg aaagacgacc catctcagtc cgctaacctg ctggcggaag caaagaagct    240
gaacgatgca caggcgccga aacatcatca ccatcaccac taataaggat cc            292
```

<210> SEQ ID NO 32
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgccagaa gaacaacgca acggtttcat    180
tcagagcctg aaagacgacc catctcagtc cgctaacctg ctggcggaag caaagaagct    240
gaacgatgca caggcgccga aacatcatca ccatcaccac taataaggat cc            292
```

<210> SEQ ID NO 33
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgtgggaa gaacaacgca acggtttcat    180
tcagagcctg aaagacgacc catctcagtc cgctaacctg ctggcggaag caaagaagct    240
gaacgatgca caggcgccga aacatcatca ccatcaccac taataaggat cc            292
```

<210> SEQ ID NO 34
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gaattctaat acgactcact ataacgcgtc cacaacggtt ccctctaga aataattttg     60 tttaacttta agaaggagat atacatatgg cagacaataa gttcaataaa gagcagcaga    120
acgcatttta cgagatcctg ctctgccgaa cctgcgcgaa gaacaacgca acggtttcat    180
tcagagcctg aaagacgacc catctcagtc cgctaacctg ctggcggaag caaagaagct    240
gaacgatgca caggcgccga aacatcatca ccatcaccac taataaggat cc            292
```

<210> SEQ ID NO 35
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gaattctaat acgactcact ataacgcgtc cacaacggtt tccctctaga aataattttg    60
tttaacttta agaaggagat atacatatgg cagacaataa gttcaataaa gagcagcaga   120
acgcatttta cgagatcctg ctctgccgaa cctggtggaa gaacaacgca acggtttcat   180
tcagagcctg aaagacgacc catctcagtc cgctaacctg ctggcggaag caaagaagct   240
gaacgatgca caggcgccga acatcatca ccatcaccac taataaggat cc            292
```

<210> SEQ ID NO 36
<211> LENGTH: 292
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gaattctaat acgactcact ataacgcgtc cacaacggtt tccctctaga aataattttg    60
tttaacttta agaaggagat atacatatgg cagacaataa gttcaataaa gagcagcaga   120
acgcatttta cgagatcctg ctctgccgaa cctgttggaa gaacaacgca acggtttcat   180
tcagagcctg aaagacgacc catctcagtc cgctaacctg ctggcggaag caaagaagct   240
gaacgatgca caggcgccga acatcatca ccatcaccac taataaggat cc            292
```

<210> SEQ ID NO 37
<211> LENGTH: 292
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
gaattctaat acgactcact ataacgcgtc cacaacggtt tccctctaga aataattttg    60
tttaacttta agaaggagat atacatatgg cagacaataa gttcaataaa gagcagcaga   120
acgcatttta cgagatcctg ctctgccgaa cctgtacgaa gaacaacgca acggtttcat   180
tcagagcctg aaagacgacc catctcagtc cgctaacctg ctggcggaag caaagaagct   240
gaacgatgca caggcgccga acatcatca ccatcaccac taataaggat cc            292
```

<210> SEQ ID NO 38
<211> LENGTH: 292
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
gaattctaat acgactcact ataacgcgtc cacaacggtt tccctctaga aataattttg    60
tttaacttta agaaggagat atacatatgg cagacaataa gttcaataaa gagcagcaga   120
acgcatttta cgagatcctg ctctgccgaa cctgcacgaa gaacaacgca acggtttcat   180
tcagagcctg aaagacgacc catctcagtc cgctaacctg ctggcggaag caaagaagct   240
gaacgatgca caggcgccga acatcatca ccatcaccac taataaggat cc            292
```

<210> SEQ ID NO 39
<211> LENGTH: 292
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 39
gaattctaat acgactcact ataacgcgtc cacaacggtt ccctctaga aataattttg      60 tttaacttta agaaggagat atacatatgg cagacaataa gttcaataaa gagcagcaga    120
acgcatttta cgagatcctg ctctgccgaa cctgaaagaa gaacaacgca acggtttcat    180
tcagagcctg aaagacgacc catctcagtc cgctaacctg ctggcggaag caagaagct     240 gaacgatgca caggcgccga acatcatca ccatcaccac taataaggat cc             292

<210> SEQ ID NO 40
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gaattctaat acgactcact ataacgcgtc cacaacggtt ccctctaga aataattttg      60 tttaacttta agaaggagat atacatatgg cagacaataa gttcaataaa gagcagcaga    120
acgcatttta cgagatcctg ctctgccgaa cctggacgaa gaacaacgca acggtttcat    180
tcagagcctg aaagacgacc catctcagtc cgctaacctg ctggcggaag caagaagct     240 gaacgatgca caggcgccga acatcatca ccatcaccac taataaggat cc             292

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, t, g, unknown or other

<400> SEQUENCE: 41
ctgccgaacc tgaacnnsga acaacgcaac gg                                   32

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5

<210> SEQ ID NO 43
<211> LENGTH: 58
<212> TYPE: PRT
<213> ORGANISM: Staphylococcus aureus
<220> FEATURE:
<221> NAME/KEY: MOD_RES
<222> LOCATION: (29)..(29)
<223> OTHER INFORMATION: Any amino acid other than Ala or Trp
```

```
<400> SEQUENCE: 43

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Xaa Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 44
<211> LENGTH: 58
<212> TYPE: PRT
<213> ORGANISM: Staphylococcus aureus
<220> FEATURE:
<221> NAME/KEY: MOD_RES
<222> LOCATION: (29)..(29)
<223> OTHER INFORMATION: Any amino acid other than Ala or Trp

<400> SEQUENCE: 44

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Xaa Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys
        50                  55
```